United States Patent
Kang et al.

(10) Patent No.: US 8,563,328 B2
(45) Date of Patent: Oct. 22, 2013

(54) FIBER-OPTIC BIOSENSOR AND BIOSENSING METHODS

(75) Inventors: Kyung Aih Kang, Louisville, KY (US); Chong H. Ahn, Cincinnati, OH (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 830 days.

(21) Appl. No.: 11/355,467

(22) Filed: Feb. 16, 2006

(65) Prior Publication Data

US 2006/0286680 A1 Dec. 21, 2006

Related U.S. Application Data

(63) Continuation-in-part of application No. 11/190,199, filed on Jul. 26, 2005, now Pat. No. 7,871,573.

(60) Provisional application No. 60/590,992, filed on Jul. 26, 2004, provisional application No. 60/653,543, filed on Feb. 16, 2005.

(51) Int. Cl.
*G01N 33/543* (2006.01)

(52) U.S. Cl.
USPC ........... 436/518; 385/12; 422/82.11; 435/7.5; 435/288.7; 435/808; 435/973; 436/172; 436/514; 436/524; 436/525; 436/527; 436/531; 436/805

(58) Field of Classification Search
USPC .................................. 435/7.1, 7.94; 436/172
See application file for complete search history.

(56) References Cited

U.S. PATENT DOCUMENTS

| | | | |
|---|---|---|---|
| 4,528,267 A * | 7/1985 | Calenoff et al. ............. | 435/7.92 |
| 4,622,291 A | 11/1986 | Picciolo et al. | |
| 4,931,385 A * | 6/1990 | Block et al. .................. | 435/7.94 |
| 5,316,909 A | 5/1994 | Xu | |
| 5,327,225 A * | 7/1994 | Bender et al. ................. | 356/445 |
| 5,373,093 A | 12/1994 | Vallarino et al. | |

(Continued)

FOREIGN PATENT DOCUMENTS

WO WO 2004/046100 A2 6/2004

OTHER PUBLICATIONS

Davies et al., "Introduction to Immunoassay Principles," The Immunoassay Handbook, $2^{nd}$ edition, Ed. by David Wild, Nature Publishing Group, 2001, New York, NY.*

(Continued)

*Primary Examiner* — Chris L Chin
(74) *Attorney, Agent, or Firm* — Greer, Burns & Crain, Ltd.

(57) ABSTRACT

A method for biosensing that includes passing, via convective flow, a sample believed to contain one or more target biomarkers through a microfluidic channel and over the surface of an optical waveguide that has been prepared to bind the one or more target biomarkers, and sensing for an emission output from the optical waveguide at a wavelength that is characteristic of the binding of the target biomarker. A biosensor device that includes a module defining at least one microfluidic channel, an optical waveguide exposed along at least a portion of its length to fluid flow within the microfluidic channel, where a surface of the optical waveguide being prepared to bind a target biomarker, and an excitation source to couple an excitation wavelength of light into the optical waveguide. The device also includes a sensor for detecting emission light from the optical waveguide at an emission wavelength characteristic of binding of the target biomarker.

18 Claims, 24 Drawing Sheets

(56) References Cited

U.S. PATENT DOCUMENTS

| | | | |
|---|---|---|---|
| 5,527,686 A * | 6/1996 | Fitzpatrick et al. | 435/7.9 |
| 5,538,857 A | 7/1996 | Rosenthal et al. | |
| 5,601,991 A | 2/1997 | Oberhardt | |
| 5,726,026 A | 3/1998 | Wilding et al. | |
| 5,804,453 A * | 9/1998 | Chen | 436/518 |
| 5,811,250 A | 9/1998 | Solum et al. | |
| 6,048,722 A | 4/2000 | Farb et al. | |
| 6,124,138 A | 9/2000 | Woudenberg et al. | |
| 6,150,180 A * | 11/2000 | Parce et al. | 506/7 |
| 6,168,948 B1 | 1/2001 | Anderson et al. | |
| 6,200,762 B1 | 3/2001 | Zlokarnik et al. | |
| 6,329,143 B1 * | 12/2001 | Stryer et al. | 506/32 |
| 6,358,526 B1 * | 3/2002 | Mergens et al. | 424/464 |
| 6,440,748 B1 * | 8/2002 | Katerkamp et al. | 436/518 |
| 2001/0038849 A1 * | 11/2001 | Dang | 424/428 |
| 2002/0110839 A1 * | 8/2002 | Bach et al. | 435/7.9 |
| 2002/0160400 A1 * | 10/2002 | Lakowicz | 435/6 |
| 2002/0179448 A1 * | 12/2002 | Lauks | 204/600 |
| 2002/0197631 A1 | 12/2002 | Lawrence et al. | |
| 2003/0148401 A1 | 8/2003 | Agrawal et al. | |
| 2004/0018577 A1 * | 1/2004 | Emerson Campbell et al. | 435/7.93 |
| 2004/0253637 A1 | 12/2004 | Buechler et al. | |

OTHER PUBLICATIONS

Liu et al., "Passive mising in a three-dimensional serpentine microchannel," J. Microelectromechanical Systems, Jun. 2000, vol. 9, pp. 190-197.*

Lakowicz et al., "Intrinsic Fluorescence from DNA can be enhanced by metallic particles", Biochemical and Biophysical Research Communications, 2001, vol. 286, pp. 875-879.

Spiker et al., "Preliminary study of real-time fiber optic based protein C biosensor", Biotechnology and Bioengineering, 1999, vol. 66, pp. 158-163.

Ulman, "Formation and structure of self-assembled monolayer", Chem. Rev., 1996, vol. 96, pp. 1533-1554.

Frankewich, Raymond P., et al. *Evaluation of the Relative Effectiveness of Different Water-Soluble B-Cyclodextrin Media to Function as Fluorescence Enhancement Agents.* Anal. Chem. 1991, 63, 2924-2933.

Rodriguez, Javier, et al. *AM1 Study of the Ground and Excited State Potential Energy Surfaces of Symmetric Carbocyanines.* J. Phys. Chem. A 1997, 101, 6998-7006.

Ruckebusch, Cyril, et al. *Hydrolysis of haemoglobin surveyed by infrared spectroscopy: I. Solvent effect on the secondary structure of haemoglobin.* Journal of Molecular Structure 478 (1999) 185-191.

Gruber, Hermann J., et al. *Anomalous Fluorescence Enhancement of Cy3 and Cy3.5 versus Anomalous Fluorescence Loss of Cy5 and Cy7 upon Covalent Linking to IgG and Noncovalent Binding to Avidin.* Bioconjugate Chem. 2000, 696-704, vol. 11.

De, Swati, et al *Enhanced fluorescence of triphenylmethane dyes in aqueous surfactant solutions at supramicellar concentrations—effect of added electrolyte.* Spectrochimica Acta Part A (2002) 2547-25555, vol. 58.

Dubertret, Benoit, et al. Single-mismatch detection using gold-quenched fluorescent oligonucleotides. 2001 Nature Publishing Group http://biotech.nature.com, Nature Biotechnology, vol. 19, pp. 365-370.

Oswald, Bernhard, et al. *Novel Diode Laser-compatible Fluorophores and Their Application to Single Molecule Detection, Protein Labeling and Fluorescence Resonance Energy Transfer Immunoassay.* Photochemistry and Photobiology, 2001, 74(2): 237-245.

Anderson, George P., et al. *Improved fluoroimmunoassays using the dye Alexa Fluor 647 with the RAPTOR, a fiber optic biosensor.* Journal of Immunological Methods 271 (2002) 17-24.

Kwon, Hyun J., et al. *Sensing performance of protein C immuno-biosensor for biological samples and sensor minimization.* Comparative Biochemistry and Physiology Part A 132 (2002) 231-238.

Balcer, Heath I., et al. *Assay Procedure Optimization of a Rapid, Reusable Protein C Immunosensor for Physiological Samples.* Annals of Biomedical Engineering. vol. 30, pp. 141-147, 2002.

Berlier, Judith E., et al. *Quantitative Comparison of Long-wavelength Alexa Fluor Dyes to Cy Dyes: Fluorescence of the Dyes and Their Bioconjugates.* The Journal of Histochemistry & Cytochemistry vol. 51(12): 1699-1712, 2003.

Buschmann, Volker, et al. *Spectroscopic Study and Evaluation of Red-Absorbing Fluorescent Dyes.* Bioconjugate Chem. 2003, 14, 195-204.

Lakowicz, Joseph R., et al. *Release of the self-quenching of fluorescence near silver metallic surfaces.* Analytical Biochemistry 320 (2003) 13-20.

Du, Xinzhen, et al. *Comparitive study on fluorescence enhancement and quenching of europium and terbium chelate anions in cationic micelles.* Spectrochimica Acta Part A 59 (2003) 271-277.

Krenn, Joachim R. *Nanoparticle waveguides: Watching energy transfer.* Nature Publishing Group http://www.nature.com/nmat/journal/v2/n4/full/nmat865,html, Nature Materials, 2003, vol. 2 , pp. 210-211.

Hong, Bin, and Kyung A. Kang, "Biocompatible, nanogold-particle fluorescence enhancer for fluorophore mediated, optical immunosensor," Biosensors and Bioelectronics (2006), vol. 21, pp. 1333-1338.

H.J. Kwon, "Theoretical and Experimental Investigation on Sensing Performance of Protein C Immuno-optical Sensor for Physiological Samples," Dissertation, University of Louisville, May 2002, pp. 43-44.

H. I. Balcer, J. O. Spiker, K. A. Kang, "Effects of Blocking Buffers and Plasma Proteins on the Protein C Biosensor Performance," Oxygen Transport to Tissue XXIV, Proceedings of the 27th annual meeting of the International Society on Oxygen Transport to Tissue (ISOTT), Aug. 28-Sep. 2, 1999, pp. 133-141.

K. Kang, "A rapid, Multi-Analyte Immuno Biosensor with Passive Microfluidics: A Model System—Four Cardiac Marker Monitoring Device," annual report, 2004, pp. 1-9.

B. Hong, "Nanometal Particle Reagents for Sensitive, MEMS based Fiber-Optic, Multi-Analyte, Immuno-Biosensing", A Dissertation Submitted to the Faculty of the Graduate School of the University of Louisville, Department of Chemical Engineering, Louisville, KY, Table 2. Commercially available POC systems for cardiac markers and their features, Dec. 2006, pp. 23.

"A Rapid, Multi-Analyte Immuno Biosensing System with Passive Microfluidics: A Model System-Four Cardiac Marker Monitoring Device", NSF Second Year Annual Report for the year 2004-2005, pp. 1-12.

"A Rapid, Multi-Analyte Immuno Biosensing System with Passive Microfluidics: A Model System-Four Cardiac Marker Monitoring Device", NSF Third Year Annual Report for the year 2005-2006, pp. 1-14.

Hong, B., Kai, J., ren, Y., Han, J., Zou, J., Ahn, C.H., and Kang, K.A., "Highly Sensitive, Rapid, Reliable, and Automatic, Cardiovascular Disease Diagnosis with Nanoparticle Fluorescence Enhancer and MEMS", Proceeding of the 2006 Annual Conference on the International Society of Oxygen Transport to Tissue, Aug. 2006, pp. 1-9.

Kai, J., Zou, Z., Han, J., Lee, L., Hong, B., Ren, Y., Kang, K.A., and Ahn, C.A., "Automated Fluidic System with a Chaotic Microfluidic Reaction Chamber for Rapid, Multi-Analyte Immuno-Sensing", Proceeding of the Annual Conference of the 14th Transducers and the 21st Eurosensors, Jun. 10-14, 2007, Lyon, France.

B. Hong, "Nanometal Particle Reagents for Sensitive, MEMS based Fiber-Optic, Multi-Analyte, Immuno-Biosensing", A Dissertation Submitted to the Faculty of the Graduate School of the University of Louisville, Department of Chemical Engineering, Louisville, Dec. 2006, pp. 1-194.

B. Hong, L. Tang, Y. Ren, K. A. Kang, "Real-time Automated, Fluorophore Mediated Multi-cardiac Marker Biosensing System with Nano-metallic Particle Reagent," Proceedings of the 33rd ISOTT Annual Meeting, Aug. 28-Sep. 2, 2005, Brisbane, Australia, pp. 1-6.

K. A. Kang, C. Ahn, "A Rapid, Multi-Analyte Immuno Biosensing System with Passive Microfluidics: A Model System-Four Cardiac Marker Monitoring Device", Proposal to The National Science Foundation, Mar. 6, 2003, pp. 1-19.

(56) References Cited

OTHER PUBLICATIONS

L. Tang, Y. Ren, B. Hong, K. A. Kang, "A fluorophore-mediated, Fiber-optic, Multi-analyte, Immuno-sensing System for Rapid Diagnosis and Prognosis of Cardiovascular Diseases", Journal of Biomedical Optics, vol. 11(2), Mar./Apr. 2006, pp. 021011-1-021011-10.

Kang, "Rapid, Multi-Analyte Immuno Biosensor with Passive Microfluidics: A Model System—Four Cardiac Marker Monitoring Device." Proposal to National Science Foundation, Mar. 6, 2003.

Kang, "A Rapid, Multi-Analyte Immuno Biosensor with Passive Microfluidics: A Model System—Four Cardiac Marker Monitoring Device." The First Annual Report, Jan. 1, 2004.

Spiker et al., "Preliminary Study of Real-Time Fiber Optic Based Protein C Biosensor." Biotechnology & Bioengineering, 1999, vol. 66, pp. 158-163.

Davies, "Introduction to Immunoassay Principles." The Immunoassay Handbook, 2nd Edition, Nature Publishing Group, 2001, New York, NY, pp. 3-40.

Ulman, "Formation and Strtucture of Self-Assembled Monolayers." Chem. Rev. 1996, vol. 96, pp. 1533-1554.

Thomas, K. George and Kamat, Prashant V., "Making Gold Nanoparticles Glow: Enhanced Emission from a Surface-Bound Fluoroprobe," J. Am. Chem. Soc. 2000, vol. 122, No. 11, pp. 2655-2656.

\* cited by examiner

TABLES

Table 1. Clinically significant sensing ranges of the anticoagulants and cardiac markers.

|  | Biomarkers | Normal Concentration [μg/ml (nM)] | Target Sensing Range [μg/ml (nM)] |
|---|---|---|---|
| Anticoagulant | PC | 4 (64) | 0.5-2.5 (8-40) |
|  | PS | 10 (143) | 1.5-5 (21-70) |
|  | ATIII | 150 (2300) | 45-105 (700-1600) |
|  | PLG | 200 (2000) | 60-120 (600-1200) |
| Cardiac marker | BNP | <0.01 (0.026) | 0.1-1 (0.026-0.26) |
|  | cTnI | <0.01 (0.03) | 0.7-7 (0.03-0.3) |
|  | MG | <30 (1.7) | 70-700 (4-40) |
|  | CRP | <800 (6.4) | 700-7000 (5.6-56) |

FIG. 6

FIBER-OPTIC BIOSENSOR AND BIOSENSING METHODS

REFERENCE TO RELATED APPLICATION AND PRIORITY CLAIM

This application is a continuation-in-part of application Ser. No. 11/190,199, filed Jul. 26, 2005 now U.S. Pat. No. 7,871,573, and entitled "Enhancement of Sensitivity of Fluorophore Mediated Biosensing and Bioimaging," which in turn claims the benefit under 35 U.S.C. §119 of earlier filed provisional application Ser. No. 60/590,992, filed Jul. 26, 2004. Priority is claimed from that application under 35 U.S.C. §120.

This application also claims the benefit under 35 U.S.C. §119 from co-pending provisional application serial number Ser. No. 60/653,543, filed Feb. 16, 2005.

STATEMENT OF GOVERNMENT INTEREST

This invention was made with Government support under BES0330075 awarded by the National Science Foundation. The Government has certain rights in the invention.

FIELD OF THE INVENTION

The field of the invention is biosensors. A particular application of the invention is simultaneously detecting and quantifying one or more target biomarkers associated with a particular disease for rapid disease diagnosis and prognosis.

BACKGROUND OF THE INVENTION

Detection of target biomarkers permits the diagnosis and prognosis of a particular disease associated with the target biomarkers. Cardiovascular Disease (CVD), which includes coronary heart disease (CHD) and venous thrombo-embolism (VTE), is the leading cause of death in the United States, with an average of one death every 34 seconds and an associated cost of approximately $400 billion.

Among the CVD related illnesses, CHD is the single largest killer of Americans. Early and accurate diagnosis of CHD, especially in an emergency room setting, is crucial to design an appropriate patient care strategy. By measuring the levels of particular biomolecules, especially multiple biomolecules simultaneously, e.g., multiple cardiac markers simultaneously, in the blood, emergency room physicians can quickly determine whether patients have actually suffered a coronary event.

Several important cardiac marker proteins have been identified and routinely used in the current clinical practice. For example, cardiac troponin I (cTnI) is widely used as a standard biomarker based on its absolute cardiac specificity and its long serum half-life (7-10 days). Additionally, a rapid increase of myoglobin (MG) level in bloodstream following heart attack allows for a rapid patient evaluation. B-type natriuretic peptide (BNP) is useful for the emergency diagnosis of heart failure and for the prognosis in patients with acute coronary syndromes (ACS). C-reactive protein (CRP) is an important prognostic indicator of CHD and ACS.

Similarly, detection of VTE or for a heightened risk of VTE may be accomplished by monitoring and quantifying levels of particular anticoagulants in a patient's bloodstream. VTE is the third leading cause of CVD, affecting 1 per 1000 persons (1% in the elderly) and includes deep vein thrombosis, lung embolism, cerebral venous thrombosis, and purpura fulminans.

When the haemostatic system in human body is unregulated, due to either coagulation problem, or more commonly, due to impaired capacity of natural anticoagulant mechanism caused by anticoagulant deficiencies, the body has a predisposition to fatal venous thrombo-embolism. Protein C (PC), protein S (PS), antithrombin III (ATIII), and plasminogen (PLG) are four major anticoagulants in blood. Deficiency in PC, PS, or ATIII was reported to significantly increase the risks of VTE, and altogether account for about 15-20% of VTE cases. Therefore, accurate diagnostic tools for early detection of these deficiencies are invaluable to prevent the fatal VTE complications and a simultaneous quantification of these four anticoagulants in blood is beneficial for the accurate diagnosis of the actual cause of an abnormal clotting.

Due to the extremely low levels of the biomarkers (pM~nM) associated with both CHD and VTE, as well as the presence of other structurally similar biomolecules in blood, a frequently used assay method is enzyme linked immunosorbent assay (ELISA). Although very accurate, it is time-consuming (hours to days), expensive, and technically complicated. Commercially available test kits for anticoagulants, BNP, cTnI, and CRP can provide fast, easy, and point-of-care assays. However, they usually provide only qualitative single biomarker information and most of the assay kits are relatively expensive, and may only be used a single time.

TABLE OF ACRONYMS
A number of acronyms are used in this application. The following table of acronyms will aid readers of this application.

| | |
|---|---|
| NGPR | Nanogold Particle Reagent |
| NMPR | Nanometal Particle Reagent |
| SAM | Self-Assembled Monolayer |
| NGP-SAM | Nanogold Particle with Self-Assembled Monolayer |
| VTE | Venous Thrombo-Embolism |
| CVD | Cardiovascular Disease |
| PC | Protein C |
| PS | Protein S |
| ATIII | Antithrombin III |
| PLG | Plasminogen |
| CHD | Coronary Heart Disease |
| cTnI | Cardiac troponin I |
| MG | Myoglobin |
| BNP | B-type natriuretic peptide |
| ACS | Acute coronary syndromes |
| CRP | C-reactive protein |

SUMMARY OF THE INVENTION

Embodiments of the invention include a biosensing method for simultaneously detecting and quantifying one or more target biomarkers associated with a particular disease for rapid disease diagnosis and prognosis. The method includes providing at least one optical waveguide, such as one or more optical sensing fibers, upon which at least one optical waveguide a fluorophore mediated sandwich immunoassay is conducted. Where multiple optical waveguides are provided, the optical waveguides are coupled to one another in series. Ends of the optical sensing fibers are optimized for the fluorophore mediated sandwich immunoassay, where 1° and 2° monoclonal antibodies (Mabs) are provided to correspond to a particular target biomarker. Observing fluorescence emission indicates the presence and quantity of the target biomarkers.

Embodiments of the invention additionally and advantageously include using convective flow to expose a sample and any associated reagents to the optical waveguides, which optimizes sensing and shortens assay times.

Additionally, fluorescence enhancers may be provided with embodiments of the invention to enhance fluorescence where the target sensing ranges of a particular biomarker are otherwise relatively low. Fluorescence enhancement includes placing a nanometal particle at a particular distance from a fluorophore to enhance fluorescence emission of the fluorophore.

Other embodiments of the invention include a biosensor that may be used to simultaneously detect and quantify one or more target biomarkers associated with a particular disease for highly accurate but rapid disease diagnosis and prognosis. Generally, the biosensor includes one or more optical waveguides, such as optical sensing fibers. In one embodiment, four optical sensing fibers are provided, coupled in series. The optical sensing fibers include ends that are tapered and otherwise configured to have a fluorophore mediated sandwich immunoassay conducted thereon.

BRIEF DESCRIPTION OF THE DRAWINGS

FIG. 6 is a table illustrating clinically significant sensing ranges of the anticoagulants and cardiac markers;

DETAILED DESCRIPTION OF EXEMPLARY EMBODIMENTS

Figure 1:
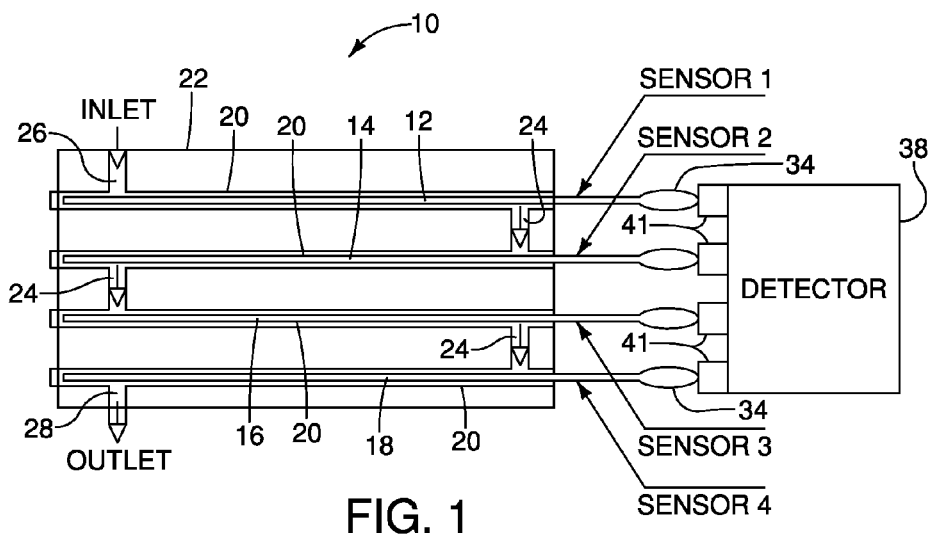
FIG. 1 is a schematic diagram illustrating a multiple biomarker biosensor according to one preferred embodiment of the invention.

To obtain accurate, rapid, and cost-effective disease diagnosis and prognosis, the invention provides for simultaneously detecting and quantifying one or more biomarkers, thereby permitting physicians, researchers and other personnel to accurately but quickly identify cardiovascular diseases and/or cardiac events. An optical waveguide, fluorophore mediated, multi-analyte immuno-biosensing method and biosensing device are provided by embodiments of the invention, and afford medical and other personnel with an invaluable diagnostic and prognostic tool.

While it is contemplated that embodiments of the invention may be used to detect and quantify a multitude of cardiovascular biomarkers and analytes, for purposes of illustration, embodiments of the invention will be shown and described in connection with other disease-representing biomarkers, as well as food, environmental and safety/security related markers. More particularly, while the invention should not be construed as being limited to biomarkers associated with cardiovascular disease, embodiments of the invention will be illustrated with reference to those biomarkers associated with coronary heart disease, acute coronary syndromes, and venous thrombo-embolism.

Embodiments of the invention provide a biosensor and biosensing methods for simultaneously sensing various biomarkers associated with cardiovascular disease, specifically coronary heart disease and venous thrombo-embolism.

Using one or more optical waveguides configured according to various embodiments of the invention, a fluorophore mediated sandwich immunoassay is conducted on surfaces of the one or more optical waveguides within evanescent wave fields of the one or more optical waveguides with a particular assay method of the invention. While the invention contemplates use of variously configured waveguides, the optical waveguides will be shown and described as generally cylindrical optical sensing fibers. It should be appreciated, however, that alternative configurations are also anticipated, including planar waveguides and other suitable waveguides.

First (1°) and second (2°) antibodies specific to a particular target analyte or biomarker are used with each of the respective one or more optical sensing fibers such that each of the optical sensing fibers binds a particular target analyte or biomarker. The 2° antibodies are tagged with a fluorophore. Thus, each optical sensing fiber is configured to detect a particular biomarker, and by providing multiple optical sensing fibers within a single biosensor, the biosensor can detect multiple analytes or biomarkers. By measuring the fluorescence emission signal from the optical sensing fibers, detection and quantification of each of the target biomarkers is possible, thereby promoting rapid and accurate diagnosis and prognosis of a disease or condition.

Embodiments of the invention provide for simultaneous detection of multiple biomarkers, which is especially advantageous where specificity of diagnosis and prognosis is enhanced with detection and quantification of multiple disease-representing biomarkers. For example, simultaneous detection and quantification of four cardiac markers, cardiac troponin I (cTnI), myoglobin (MG), B-type natriuretic peptide (BNP) and C-reactive protein (CRP), are important to accurate and highly specific diagnosis and prognosis of cardiovascular disease. Similarly, simultaneous detection and quantification of four anticoagulants, Protein C (PC), protein S (PS), antithrombin III (ATIII), and plasminogen (PLG), are important to accurate diagnosis for the cause of the symptoms, i.e., venous thrombo-embolism (VTE). Thus, embodiments of the invention providing multiple optical sensing fibers are especially advantageous in providing simultaneous detection and quantification of multiple biomarkers or other analytes.

By applying the sample and any associated reagents via convective flow through the biosensor, as well as by using various signal enhancers, embodiments of the invention are particularly advantageous in that assay time is relatively short, being on the order of approximately 5 minutes, which renders the invention especially amenable for use at a patient's bedside or in an emergency room setting. Compared to the conventional analytical methods such as DNA analysis, polymerase chain reaction, high performance liquid chromatography, and ELISA, the immuno-optical biosensor has the advantages of rapid response time, user-friendliness, and cost-effectiveness. Additionally, other embodiments of the invention provide an automatic, self-contained and portable sensing device. Furthermore, embodiments of the invention include high sensor reusability and low background signals.

Turning now to FIG. 1, a preferred biosensor, designated generally at 10, includes a plurality of optical sensing fibers 12, 14, 16, 18, which are fluidly coupled in series to one another and at least partially disposed within microchannels 20 of a sensor housing 22. While it is contemplated that embodiments of the biosensor may include a various numbers of optical sensing fibers, exemplary embodiments are primarily shown and described with detection and quantification of VTE and CVD, and as such, will be shown and described with four optical sensing fibers associated with the four disease-representing biomarkers associated with each respective disease. However, it should be appreciated that the biosensor 10 may include both fewer than four and more than four optical sensing fibers, as the number of optical sensing fibers may vary to suit individual applications.

A plurality of communication channels 24 maintain fluid communication between the optical sensing fibers 12, 14, 16, 18, as well as promoting maintenance of flow direction. At least one inlet 26 and one outlet 28 are provided for introducing sample or other fluids and for expelling same.

The optical sensing fibers 12, 14, 16, 18 are preferably quartz owing to the high quality signal and less optical noise and background signal provided by the quartz fibers. Additionally, while the invention contemplates use of various constituent materials for the optical sensing fibers, one preferred material is quartz because it promotes regeneration and is compatible with various reagents used with embodiments of the invention. However, it should be appreciated that other materials are suitable for use with the invention, preferably those materials that also promote regeneration of the optical fiber sensors, and are compatible with various reagents used in embodiments offe the invention.

Additionally, the fibers 12, 14, 16, 18 have a predetermined length that is optimized to be the shortest length having a reasonable signal-to-noise-ratio (S/N ratio), preferably higher than 8. While it is anticipated that a length of the optical sensing fibers can be selected to suit individual applications, a smaller optical sensing fiber is relatively easier to handle, more portable, and also requires less sample and reagent volume (i.e., less expense for a single assay). Accordingly, exemplary lengths of the preferred optical sensing fibers are from between approximately 1.5 cm and 12.5 cm.

Figure 2:
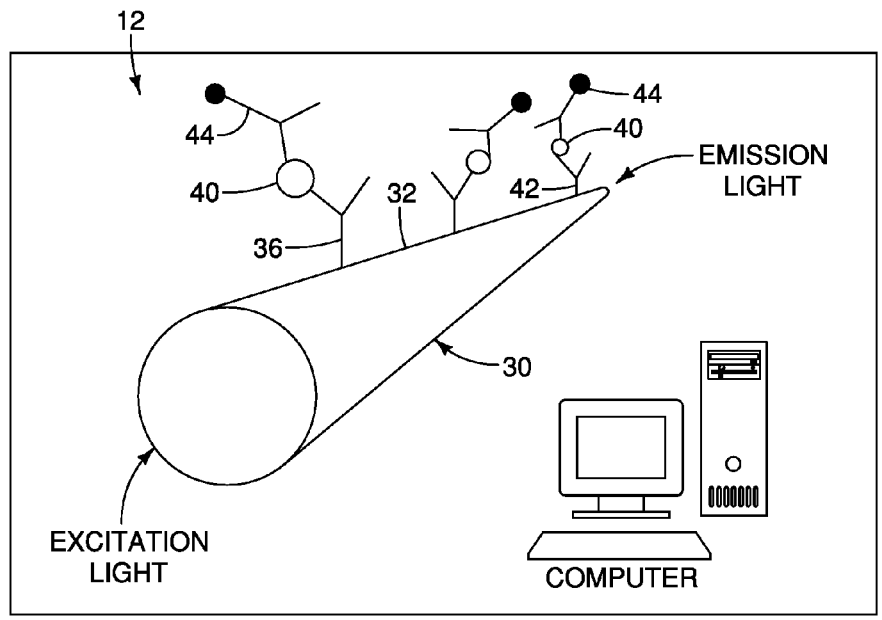
FIG. 2 is a schematic diagram illustrating an optical sensing fiber with a sandwich immunoassay disposed thereon.

As illustrated in FIG. 2, a fluorophore mediated sandwich immunoassay is conducted within an evanescent wave field of each of the four optical sensing fibers 12, 14, 6, 18, and the optical sensing fibers are preferably configured and prepared to optimize the assay. To this end, each of the four optical sensing fibers 12, 14, 16, 18 is preferably configured to have an optimized sensing end, generally at 30, where the cladding is removed to expose a core, and which is further tapered such that a circumference of the optical sensing fibers gradually decreases in size. The use of the optimized sensing ends 30 is preferred as it has been shown to increase signal retrieval from the optical sensing fibers 12, 14, 16, 18.

The optimized sensing end 30 can be achieved, for example, by removing cladding at a predetermined length from first ends of the fibers and then etching the exposed fiber core 32, for example with hydrofluoric acid or another suitable etchant. The taper can be achieved by various methods, including, for example, using an automatic tapering machine. The optimized sensing ends 30 are then preferably chemically treated to be streptavidin-coated.

Referring again to FIG. 1, the optical sensing fibers 12, 14, 16, 18 have their optimized sensing ends 30 disposed at least partially within the respective microchannels 20 to enclose a length of the optimized sensing ends within the sensor housing 22, with opposite ends 34 extending outwardly of the sensor housing. More particularly, in the preferred embodiment, the optimized sensing ends 30 are enclosed within the sensor housing 22, with the remainder of a length of the optical sensing fibers 12, 14, 16, 18 extending externally to the sensor housing and coupling the optical sensing fibers to an emission detector. Inner surfaces of the sensor housing 22 and, particularly the microchannels and communication channels 24 preferably, though not necessarily, include a coating, such as Sigmacote®, to reduce adsorption of the biomarkers or other analytes during the assay. Two nylon T connectors 35 are provided at either end of the sensor housing 20.

A sample to be analyzed, such as blood plasma, is introduced to the biosensor 10 via the inlet 26. Convective flow of the sample through the biosensor 10 is preferably employed to enhance the mass transport of the biomarkers from the bulk media (e.g., plasma) to the surface of the optical sensing fibers 12, 14, 16, 18 to improve sensing performance and to shorten the assay time significantly. In one embodiment, a microfluidic unit, such as a pump 36 (FIGS. 22-24), is provided for flow velocity control.

Thus, using FIG. 1, for the simultaneous multiple-biomarker quantification, such as four-anticoagulant or four cardiac marker quantification, each optical sensing fiber 12, 14, 16, 18 includes 1° Mabs 37 against one of four respective anticoagulants or cardiac markers immobilized on its surface by avidin-biotin bonding. Each optical sensing fiber 12, 14, 16, 18 is placed in one of the four microchannels 20 in the four-analyte biosensor 10. The biosensor 10 connects the four optical fiber sensors 12, 14, 16, 18 in series, and when a sample flows over the four microchannels 20, each anticoagulant is captured by one of the four optical sensing fibers for detection. The optical sensing fibers 12, 14, 16, 18 are highly specific with little cross-reactivity.

Fluorescence emission is measured via a fluorometer 38 operably coupled to the biosensor 10. Separate detectors are preferably provided within the fluorometer 38 for the individual signals emitted from the individual optical sensing fibers 12, 14, 16, 18. In the exemplary embodiment, four separate detectors are provided in the fluorometer 38 to detect the four different signals from the four optical sensing fibers 12, 14, 16, 18, where one of the respective fibers is disposed in one of a corresponding one of the four microchannels 20. Excitation light from a laser diode, e.g., 636 nm, can be coupled into the optical sensing fibers 12, 14, 16, 18. 2° Mabs 39, which are tagged with a fluorophore and bound to the biomarkers 40, interact with the evanescent wave of the excitation light to generate an emission signal at a characteristic wavelength, e.g., approximately 667 nm, that is different from the excitation wavelength. Detecting emitted light indicates the presence of the biomarker of interest. The strength of the characteristic wavelength correlates with the concentration of the biomarker of interest in the sample.

An example method for detection of the characteristic wavelength or wavelengths of interest is to pass output of the optical sensing fibers 12, 14, 16, 18 through a bandpass filter 41 and detect the filter's output with the photodetector 38. Finally, the intensity of fluorescence is correlated with a concentration of the biomarker 40. The presence or absence of each of the respective biomarkers 40, as well as the quantities of each, may thus be determined to enable physicians and other clinicians to quickly and accurately determine the presence of a disease or coronary event.

Optionally, the preferred embodiment may include novel fluorescence enhancers to enhance the fluorescence emission, thereby optimizing sensitivity of the optical sensing fibers 12, 14, 16, 18. These fluorescence enhancers may include nanometal particles strategically juxtaposed within a predetermined distance of the fluorophore of the 2° Mabs 39, as well as using certain organic solvents containing nanometal particles to be juxtaposed at a predetermined distance of the fluorophore of the 2° Mabs.

Turning to FIG. 2, the exemplary biosensor 10 includes the four optical sensing fibers 12, 14, 16, 18, which are configured and prepared to optimize the fluorophore-mediated sandwich immunoassay used with embodiments of the invention.

More particularly, each of the optical sensing fibers 12, 14, 16, 18 are preferably chemically treated to have a streptavidin, and the 1° Mab 37 is biotin-conjugated. By reacting biotin conjugated 1° Mab 37 with the streptavidin treated fiber, 1° Mabs are immobilized via the strong streptavidin-biotin binding. Thus, the 1° Mabs 37 are provided to correspondingly bind a respective biomarker. Where, for example, the biosensor 10 is used to detect coronary heart disease, each of the optical sensing fibers 12, 14, 16, 18 can be configured to bind a respective one of cardiac troponin I (cTnI), myoglobin (MG), B-type natriuretic peptide (BNP) and C-reactive protein (CRP). Similarly, where the biosensor 10 is used to detect venous thrombo-embolism, each of the optical sensing fibers 12, 14, 16, 18 can be configured to bind a respective one of protein C (PC), protein S (PS), antithrombin III (ATIII), and plasminogen (PLG).

The target biomarker 40 binds a respective one of the 1° Mabs 37. After the optical sensing fibers 12, 14, 16, 18 are washed to remove excess biomarkers or other analytes, a fluorophore-tagged 2° Mab 39 specific to each of the target biomarkers is exposed to the optical sensing fibers. While it is contemplated that various fluorophores may be used, one exemplary fluorophore is AF647. All four of the respective AF647-2° Mabs 39 may be introduced together into the sensor 10, or separately to each respective optical sensing fiber 12, 14, 16, 18.

Additionally, as between the 1° and 2° Mabs 37, 39 the one having the lower affinity is preferably used as the 1° Mab because the lower affinity Mab will be more likely to easily elute captured antigen to a preferred regeneration step, thereby permitting multiple uses per optical sensing fiber 12, 14, 16, 18. Basic reagents, such as triethylamine (TEA) buffer for example, are especially advantageous in promoting regeneration of the optical sensing fibers 12, 14, 16, 18.

Multiple Coagulant Biosensor

While the preferred embodiment may be used to detect one or more of a variety of biomarkers and other analytes, one exemplary application includes the simultaneous detection of several anti-coagulants. Specifically, lower quantities of PC, PS, ATIII and PLG are indicative of a high risk for venous thrombo-embolism, for example, and the preferred device and method may be used in connection with quantifying of these particular biomarkers. There are a large population of a genetically inherited deficiency of these anti-coagulants.

The optical sensing fibers 12, 14, 16, 18 of the multiple anti-coagulant biosensor are optimized in accordance with target sensing ranges for the various anticoagulants, which are: PC (0.5~2.5 µg/ml; 8~40 nM), PS (1.5~5 µg/ml; 21~70 nM), ATIII (45~105 µg/ml; 700~1600 nM), and PLG (60~120 µg/ml; 600~1200 nM). Where the biosensor 10 is configured to detect and quantify multiple biomarkers, each of a plurality of optical sensing fibers 12, 14, 16, 18 are fluidly coupled in a multiple-analyte sensing unit, such as the housing 22 illustrated in FIG. 1.

Blood plasma is frequently the sample for an assay in the clinical practice, and will accordingly be discussed in connection with the instant embodiment, though it should be understood that other samples are contemplated for use with the invention.

Theoretical and experimental analyses demonstrate that the main cause for signal reduction is the relatively high viscosity of plasma. Using PC as an example, the reaction kinetics of an analyte (here, PC) and a 1° Mab 37 in a fiber-optic biosensing system involves two steps: the analyte transport from the liquid medium to the sensor surface; and the reaction between the transported analyte and the 1° Mab molecule on the surface. During the static incubation period, analyte molecules are transported to the sensor surface by diffusion. The analyte diffusion coefficient (D; cm²/s) is inversely related to the sample medium viscosity (Eq. 1):

$$D = \frac{kT}{6\pi\mu R_A} \quad (1)$$

where k, the Boltzmann constant ($1.38\times10^{-23}$ J/K); T, the sample medium temperature (room temperature, 298 K); μ, the sample medium viscosity (1.0 cP for PBS buffer and 1.9 cP for plasma); and $R_A$, the radius of the analyte. Since the viscosity of plasma (1.9 cP) is almost twice of that of the PBS, the PC diffusion coefficient in plasma is approximately 50% less. The Damkohler number ($N_{Da}$) is used for analyzing reaction kinetics: a system with an $N_{Da}$ value of greater than 100 is considered to be diffusion-limited; less than 0.01, reaction-limited. The values for the PC systems in both PBS and plasma samples are in the order of 100, indicating that the systems are diffusion-limited and the system with plasma samples is more diffusion-limited than the one with PBS buffer.

To enhance the sensing performance by improving the analyte mass transport to the sensor surface, another mechanism, in addition to diffusion, is preferably provided in the instant embodiment. By applying convective flow during the sample incubation, the biosensor performance for viscous samples (e.g. plasma) is significantly enhanced. On the surface of a sensor, there is a frictional film, resistant to the analyte mass transport from the bulk solution to the biosensor surface to react with 1° Mab immobilized on the surface. The thickness of this film (δ; cm) is closely related to the analyte mass transport rate:

$$\delta = \frac{D}{k_m} \quad (2)$$

where $k_m$ is the effective mass transfer coefficient (cm/s).

When a convective flow is applied during the incubation (reaction) of sample, the film thickness is significantly reduced. For the instant sensing system, compared to the analyte mass transport rate at 0.1 cm/s, the $k_m$ value at 0.7 and 1.2 cm/s is increased by 157 and 232%, respectively. As a result, the film thickness was reduced with the increase in the flow velocity. At 0.1 cm/s, the thickness was $12\times10^{-3}$ cm. When the flow velocity was increased to 0.7 cm/s, the film thickness was reduced by 60% ($4.5\times10^{-3}$ cm). At 1.2 cm/s, the thickness was only 30% ($3.5\times10^{-3}$ cm) of that of 0.1 cm/s. Experimental analysis shows that the signal intensity at 0.7 cm/s increased by 110% for 1 μg-PC/ml-plasma, compared to that with the static incubation. At the higher flow velocities, although the PC mass transport is even faster, the reaction rate is not fast enough to consume all of the PC molecules transported to the sensor surface. Therefore, the signal intensity remained steady at the velocities higher than 0.7 cm/s. The optimal flow velocity for the PC sensing was then determined to be 0.7 cm/s, where the reaction kinetics changes from the mass-transport-limited to the reaction-limited. At this velocity, the PC assay time was reduced to 5 minutes including 0.5 and 2 minutes for the sample and second antibody incubations, respectively.

While it is contemplated that the 2° Mab 39 may be tagged with one of a variety of fluorophores, such as Cyanine 5 (CY5™), AF647, ATTO 647, BODIPY™ 650/665 dye and DY-636, the preferred fluorophore is AF647. AF647 has a quantum yield more than twice of that of Cyanine 5 (CY5™) (0.28) and is more photostable. The excitation and emission wavelengths of AF647 are also compatible with a preferred fluorometer 42 (FIG. 10a) used with embodiments of the invention, the Analyte 2000™. It has been demonstrated that AF647 can improve the sensing performance of the fluoro-immunoassays significantly.

Figure 3:
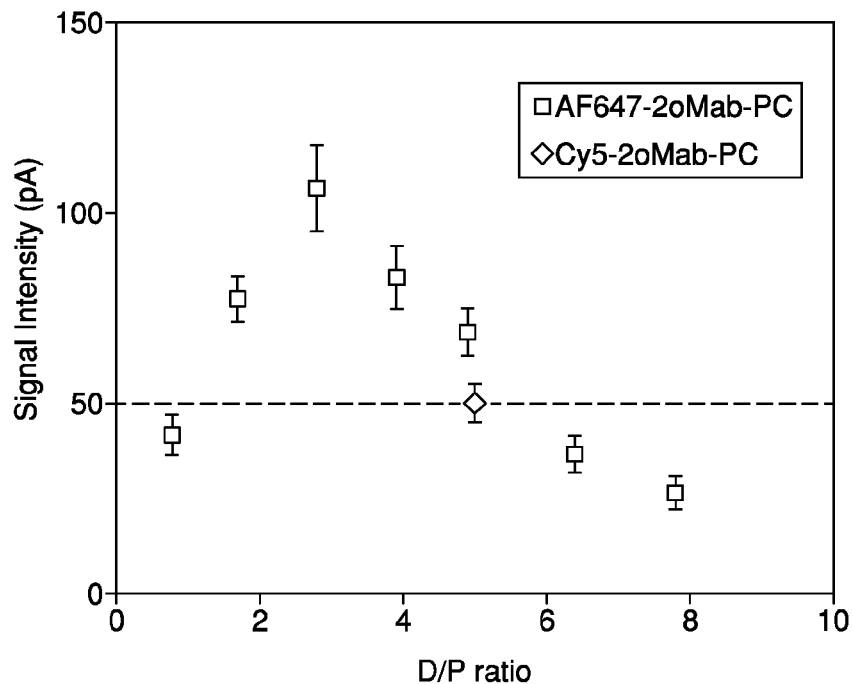
FIG. 3 is a graph illustrating cross-reactivity of PC, PS, ATIII, and PLG sensors.

To demonstrate the efficacy of the AF647-conjugated second antibody for the PC sensing, AF647 was conjugated with the 2° Mab-PC (AF647-2° Mab-PC) at various dye-to-protein (D/P) ratios from 1 to 8. 1 μg/ml PC was reacted with the 1° Mab-PC immobilized on the sensor surface and then AF647-2° Mab at various D/P ratios was applied to the sensor (FIG. 3). The signal intensity increased steadily up to the D/P ratio value of 3 and then, the signal intensity decreased with the increase in the ratio. Since the fluorescence for free forms of AF647-2° Mab at higher D/P ratios increased (data not shown), one possible reason for the signal intensity reduction in the PC sensing system is the reduced relative affinity of AF647-2° Mab to the PC at higher D/P ratios. The result from ELISA showed that, at the D/P ratio of 2 and 3, the relative affinity of AF647-2° Mab-PC was similar to the 2° Mab-PC without conjugates (i.e., D/P=0), and at D/P ratio of 4, the relative affinity of the 2° Mab-PC to PC molecules was decreased by 40%. The optimal AF647 D/P ratio for the PC sensing was, therefore, determined to be 3. The signal intensity of PC measurement using AF647-2° Mab at D/P ratio of 3 increased by approximately 115%, compared to the Cy5-2° Mab-PC at the optimal D/P ratio of 5.

In the clinical practice, a minimal bio-sample volume for an assay is desirable and therefore, the invention preferably optimizes the sensor size. The performance of a 3-cm PC optical sensing fiber was tested in the target sensing range and compared with that of a 6-cm sensor. The signal intensity of the 3-cm PC sensor also showed a linear relationship with the PC concentration, at an average signal-to-noise (S/N) ratio of approximately 25. This result demonstrated that a 3-cm PC optical sensing fiber is capable of accurately quantifying PC in plasma (sample volume: ~500 μl) in the clinically important sensing range for the PC deficiency diagnosis within 5 minutes.

Similarly, the sensing protocol of the PC sensing optical sensing fiber was further extended for the optimization of PS, ATIII, and PLG sensing. The optimal flow velocity for the PS sensing was determined to be 0.5 cm/s (data not shown), which is less than the optimal velocity of the PC sensing (0.7 cm/s for 1 μg/ml PC). It is probably because the PS sensing range is higher than the PC's and therefore, less mass-transfer-limited during the reaction between PS and 1° Mab-PS, assuming that antibodies for both systems have similar affinity to respective antigens. The effects of the convective flow on the ATIII and PLG sensing performance were also studied. Unlike the PC sensing, with a static incubation (i.e., no flow), the signal intensity was high enough to clearly differentiate ATIII or PLG concentration in the sensing range, indicating that the diffusional mass transport is sufficient for the ATIII or PLG molecular supply to the sensor surface, since the sensing ranges are hundreds of times higher than that of PC. Similar to the PC sensor, the standard curves of the PS, ATIII, and PLG sensing were in linear relationship ($r^2$=0.99) with the respective analyte concentration in the sensing ranges, at a S/N ratio of 30, capable of quantifying each concentration in the blood plasma in the deficiency range within 5 minutes.

For multi-anticoagulant sensing, after the sample incubation, four different AF647-2° Mabs 39 are introduced into the respective microchannels 20 for quantification by fluorescent signals. It is anticipated that this may be done in at least two ways, by either applying each type of fluorophore tagged 2° Mabs 39 to the respective microchannel 2°, or applying a mixture of the four different fluorophore tagged 2° Mabs through the four-analyte biosensor 10 if the mixture does not affect the sensing performance.

Figure 4:
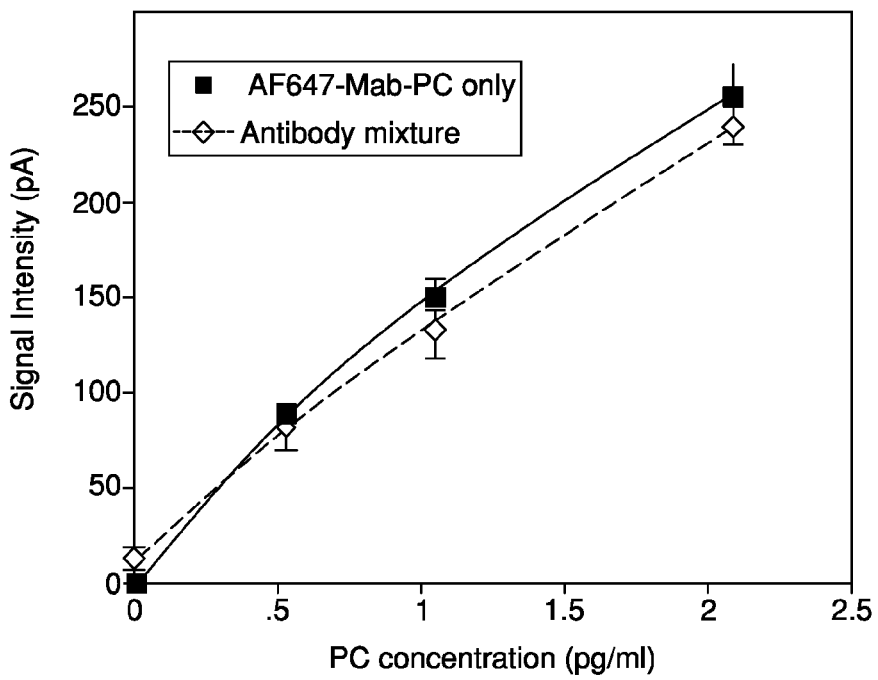
FIG. 4 is a graph illustrating an effect of the mixture of AF647-2° Mabs against PC, PS, ATIII, and PLG on PC sensing.
Figure 5A:
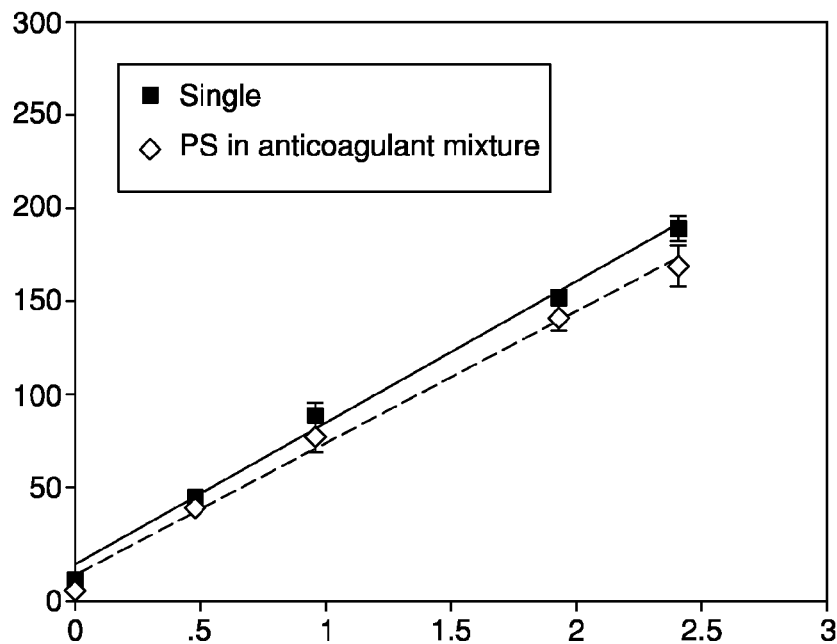
FIGS. 5A-5D are graphs respectively illustrating sensitivity of PC, PS, ATIII, and PLG sensors in a four optical sensing fiber biosensor in accordance with an embodiment of the invention for simultaneous four factor quantification.
Figure 5B:
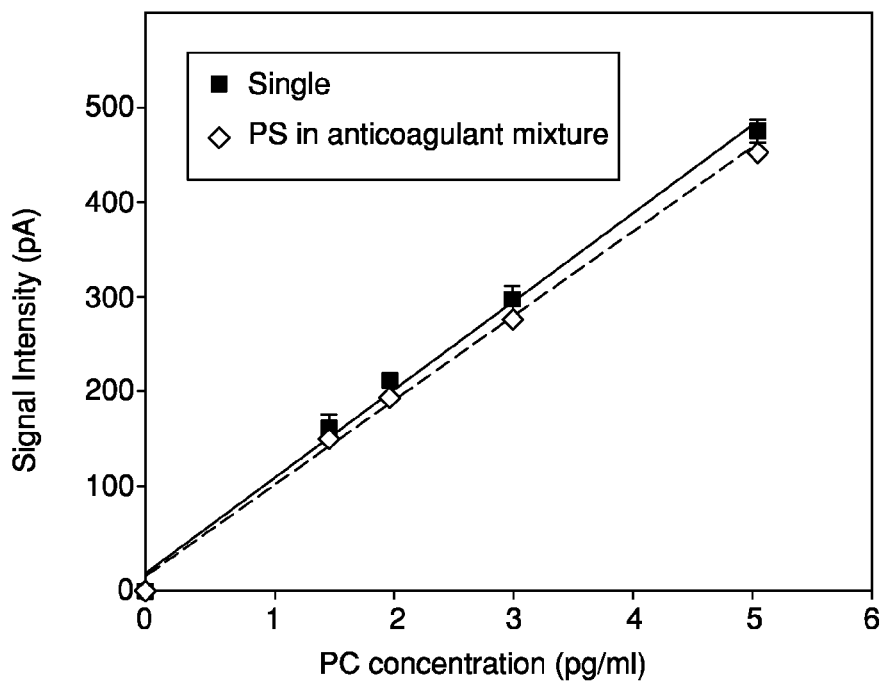
Figure 5C:
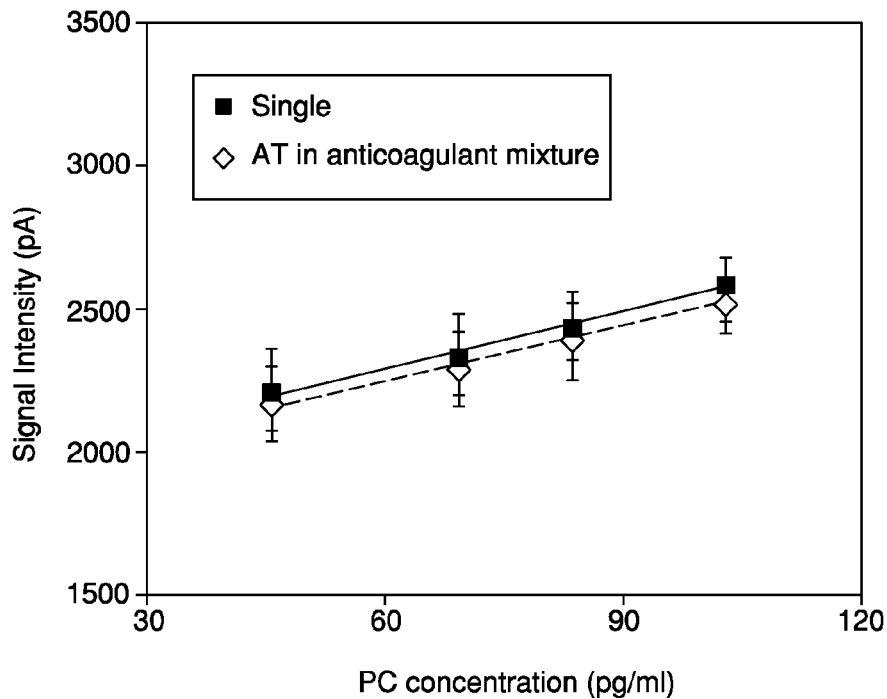
Figure 5D:
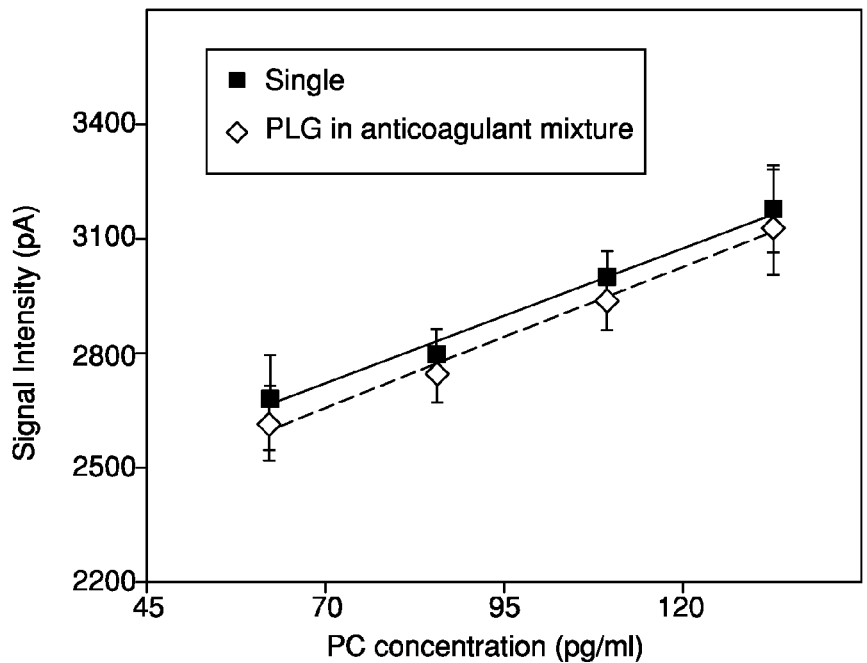

The latter is preferred because it provides an easier design for the fluid manipulation and automation of the sensing procedures, and the mixture does not significantly reduce signal intensity. FIG. 4 shows the signal intensities generated by a PC optical sensing fiber using only AF647-2° Mab-PC (■) and the AF647-2° Mabs mixture (◇). Both measurements were performed by a single PC optical sensing fiber to eliminate possible fiber-to-fiber sensing variation. The concentration of the four different AF647-2° Mabs in the mixture was four times of that of individual sensing. The signal intensity generated by the mixture slightly decreased, but the reduction was less than 6%, with a similar standard deviation (5~10%) for both measurements. The cross-reactivity among the four analytes was already proven to be minimal.

The effect of the antibody mixture on the PS, ATIII, and PLG optical sensing fiber performance was also studied. Similar to the PC optical sensing fiber, the signal intensities of the measurements with the AF647-2° Mabs mixture were slightly decreased by less than 4.5%. For all the four optical sensing fibers 12, 14, 16, 18, the standard curves with the AF647-2° Mabs mixture were linear with the respective anticoagulant concentration ($r^2$=0.99), at an average S/N ratio of 25. These results demonstrated that the simultaneous quantification of the four anticoagulants is possible with the mixed AF647-2° Mabs with little changes in the sensitivity, especially if the standard curve is also obtained with the AF647-2° Mabs mixture. Therefore, the instant embodiment preferably includes applying the AF647-2° Mabs mixture to the multi-sensing biosensor 10 for simultaneous PC, PS, ATIII, and PLG detection.

The sensitivities of the four anticoagulant optical sensing fibers 12, 14, 16, 18 in multi-sensing are similar to the individual anticoagulant sensing (FIGS. 5A-5D). The standard curves are linear with the respective analyte concentration in the sensing ranges ($r^2$=0.97~0.99). The study results demonstrated that the four-analyte biosensor 10 is capable of performing a rapid (~5 minutes), accurate, and simultaneous quantification of PC, PS, ATIII, and PLG in blood plasma, at an average S/N ratio of 25.

Multiple Cardiac Biomarker Sensing

The fiber-optic, multi-analyte immuno-biosensor 10 can also be applied for simultaneous quantification of multiple cardiac markers in blood plasma as a diagnostic and prognostic tool for coronary heart disease. As illustrated in FIG. 6, the clinically significant sensing ranges for the BNP [0.1~1 ng/ml (26~260 μM)] and cTnI [0.7~7 ng/ml (30~300 pM)] are hundreds of times lower than the anticoagulants. The MG [70~700 ng/ml (4~40 nM)] and CRP [700~7000 ng/ml (5.6~56 nM)] are comparable to the anticoagulants.

Due to the extremely low target BNP and cTnI sensing range, the instant embodiment provides optional alternatives to optimize sensitivity during the detection and quantification of these two biomarkers. For example, an optimal length of each of the optical sensing fibers 12, 14, 16, 18 may be increased, and/or incubation time may be increased. One preferred optical sensing fiber 12, 14, 16, 18 is approximately 12 cm long with an incubation period of approximately 10 minutes. Alternatively, or in combination with the optimized fiber length and incubation time is an innovative method of juxtaposing particular reagents with the optical sensing fibers 12, 14, 16, 18 to enhance fluorescence emission. Additionally, convective flow of the sample is preferably employed. While lengths of the optical sensing fibers 12, 14, 16, 18 may vary widely to suit individual applications, an exemplary range of lengths is from between approximately 1.5 cm and 3 cm, when used in connection with NMPR or NGPR.

More particularly, to illustrate with one exemplary embodiment, 12-cm BNP optical sensing fibers 12, 14, 16, 18 were provided and incubation time was increased to approximately 10 minutes, each, for the sample and AF647-2° Mab incubation. With a static incubation (i.e. no flow), the signal intensity of the BNP sensing in blood plasma was only 5~10 pA. Evaluation of the Damkohler number ($N_{Da}$) shows that the reaction kinetics of the BNP and cTnI sensing system is also mass-transfer-limited with diffusional mass transport only. To improve the sensing performance by accelerating the analyte mass transport, a convective flow was applied and the optimal flow velocity was determined to be 1.2 cm/s (FIGS. 27a-27d). This flow velocity is much higher than the anticoagulant sensing system, because of the extremely low sensing range and a thicker film. The film thickness for the BNP sensing at 0.1 cm/s was calculated to be $25.9 \times 10^{-3}$ cm, twice of that of the PC sensing system ($12 \times 10^{-3}$ cm).

The signal intensity for a biomarker, such as BNP and cTnI, was extremely low due to the low target sensing range. Since the fiber-optic biosensor 10 is fluorophore mediated, fluorescence enhancers may be applied to improve the biosensor performance by enhancing the fluorescent signal.

More particularly, the preferred multiple biomarker biosensor 10 includes novel nanometal particle reagents (NMPRs), which improve the sensitivity of the biosensor as high as 10 times. The NMPRs are specially prepared with nanometal particles in a selective, biocompatible organic solvent. While it is contemplated that numerous NMPRs may be used with the invention, reagents combined with nanogold particles and nanosilver particles will be shown and discussed for purposes of illustration. However, it should be appreciated that a variety of NMPRs, such as those combined with nanoplatinum particles and nanocopper particles, for example, may be used to suit individual applications.

Nanometal Particles, Solvents and Nanometal Particle Reagents

While several exemplary embodiments and exemplary results will be shown and described, further details of the nanometal particles, solvents, and nanometal particle reagents as they are used in connection with various embodiments of the invention may be found in published U.S. patent application Ser. No. 11/190,199, which was filed Jul. 16, 2005 and published on Feb. 2, 2006.

Figure 7A:
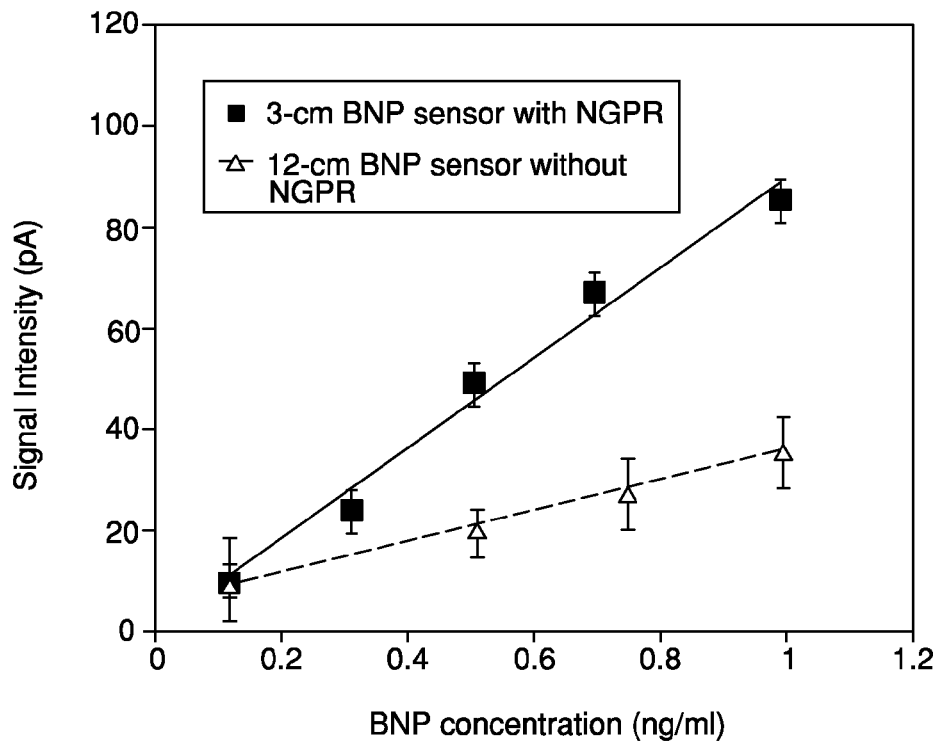
FIGS. 7A-7D are graphs respectively illustrating standard curves of BNP, cTnI, MG, and CRP sensing with (■) and without (Δ) NGPR.
Figure 7B:
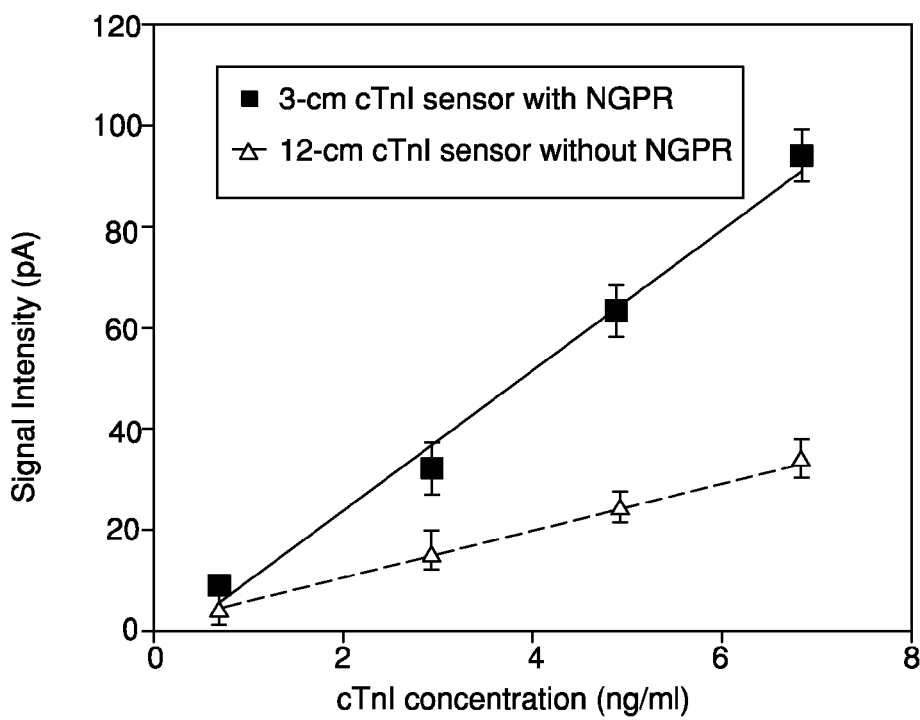
Figure 7C:
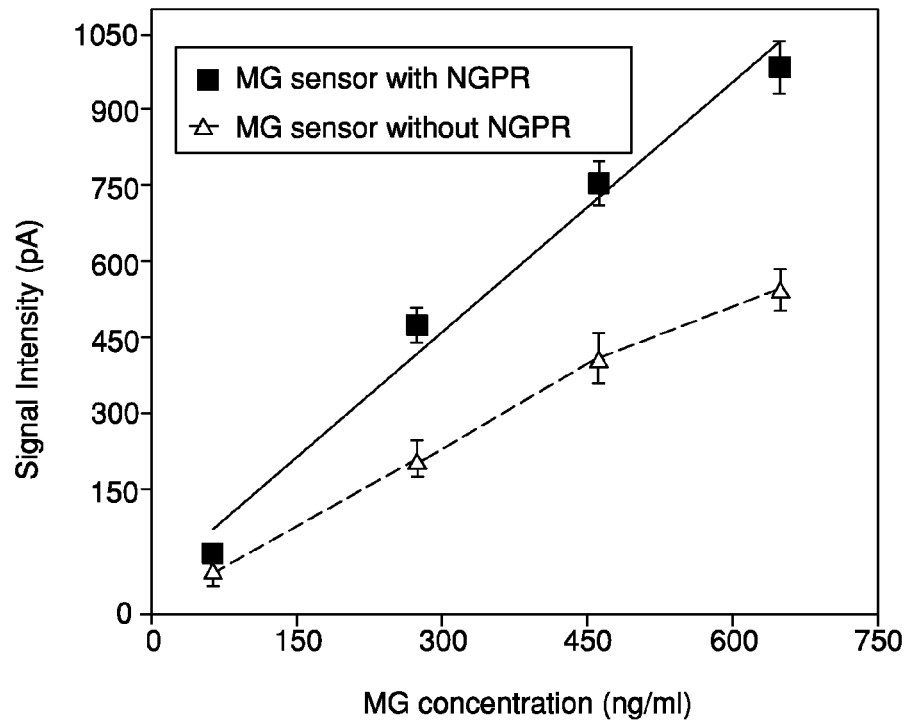

Turning to FIGS. 7A through 7D, the fluorescence enhancement is accomplished by (1) the transfer of the electrons, normally involved in intra-molecular fluorescence quenching, from a fluorophore to the nanometal particle, via the plasmon rich, electromagnetic field surrounding the nanometal particle; and by (2) the increase of the energy gap of a fluorophore between the ground and the excite states in a solvent. FIG. 7A shows the standard curve of the BNP sensing with nanogold particle reagent (NGPR). The signal intensity increased by approximately 100-300%, with the sensor size reduced by 75% and a less than 50% of the assay time. Similar results were obtained for the cTnI, MG, and CRP sensing (FIGS. 7B-7D), indicating that the 3-cm cardiac marker sensors were capable of accurately quantifying the cardiac marker concentrations in blood plasma within 10 minutes, at an average S/N ratio of 25.

Similar to multi-anticoagulant sensing, the four cardiac biomarker optical sensing fibers 12, 14, 16, 18 are preferably connected in series in a four-analyte biosensor 10 for simultaneous multi-cardiac-marker quantification. The four cardiac markers have no known structural homology. However, to determine the possible interference to the sensing performance in the multi-sensing format, each optical sensing fiber 12, 14, 16, 18 was tested with samples containing the other three analytes at their upper limit sensing ranges, as in multi-anticoagulant sensing. The signal intensities generated by the BNP sensor for cTnI (7 ng/ml), MG (700 ng/ml), and CRP (7000 ng/ml) in the sample were less than 5% of the response for the BNP at its lower sensing limit (0.1 ng/ml). Similar results were shown for the cTnI, MG, and CRP sensors when probed with the other three analytes present in the sample. AF647-2° Mabs mixture was also tested and it was found that each optical sensing fiber 12, 14, 16, 18 can be as accurate as that with only the respective AF647-2° Mab, with a slight signal reduction.

The sensing performance of the multi-cardiac-marker quantification was comparable to the single cardiac marker sensing, at a similar S/N ratio. Similar to the multi-anticoagulant sensing, the signal intensity for mixed sample was slightly decreased (5~10%) due to the presence of other three analytes in the sample. The multi-sensing biosensor 10 is capable of simultaneous quantification of the four biomarkers within 10 minutes, at an average S/N ratio of 20.

Alternative embodiments of the invention include enhancing the fluorescence emission of the fluorophore by providing a nanometal particle at a predetermined distance therefrom, providing certain organic solvents to enhance fluorescence, and/or providing a solvent having the nanometal particles disposed therein. In the alternative embodiments that include nanometal particles, the method and device include a new baseline with the enhancer, and applying the enhancer after the washing step following the surface immuno-reactions between the analyte and the fluorophore linked 2° Mab 39.

Figure 8A:
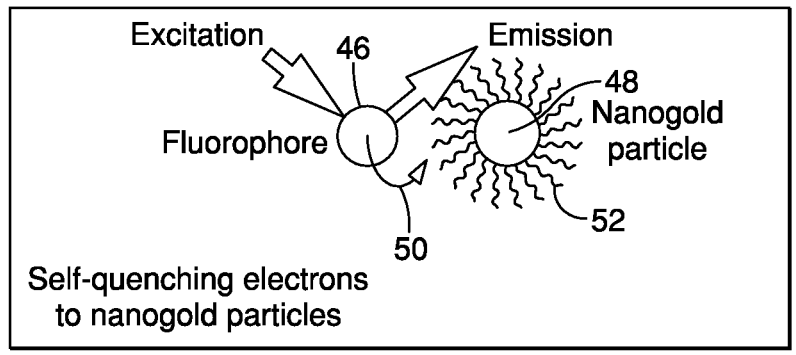
FIGS. 8A-8C are schematic diagrams respectively illustrating an effect of the distance between a fluorophore and a nanogold particle distances that are appropriate, too far apart, and too close together.

Turning to FIGS. 8Aa through 8C, when located at an appropriate distance from a fluorophore 46, plasmon rich nanometal particles, such as nanogold particles 48 and nanosilver particles (not shown), can enhance fluorescence of the fluorophore by rerouting the electrons (represented by arrow 50) that contribute to self-quenching. The efficiency of the electron transfer is dependent on several variables, such as the separation between a nanometal particle and a fluorophore, the size of the nanometal particle, and the quantum yield of a particular fluorophore.

As an effective method to control the distance between these two entities, immobilized self-assembled monolayers 52 (SAMs) having various thicknesses are disposed on the surface of the nanometal particles. The SAM may include one of a plurality of molecules, preferably those water soluble, organic molecules with a thiol or amine terminal group in their structures, that may self-assemble onto the nanoparticles. By way of example only, two such molecules are L-Glutathione and 16 mercaptohexadecanoic acid.

Figure 9:
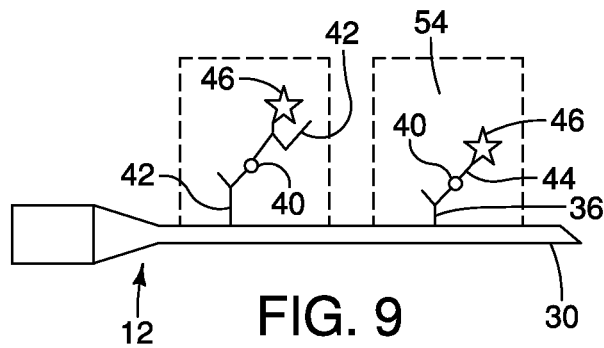
FIG. 9 is a schematic diagram illustrating one of the possible causes for the solvent effect on fluorophore mediated biosensing.

In addition, several bio-compatible solvents significantly enhance fluorescence. As illustrated in FIG. 9, this enhancement is possibly contributed by the shift of excitation/emission spectrums for the fluorophore 46, and/or by isomerization of the fluorophore, or by more fluorescence retrieval when the fluorophore tagged, sandwich protein complex shrinks in the solvent and gets closer to the sensor surface.

The quantum yield of the fluorophore 46 is solvent sensitive since the excitation/emission spectrums may exhibit red or blue shift in a different solvent. The trans/cis isomerization of the fluorophore 46 in the solvent may also cause the fluorescence enhancement. Therefore, fluorescence enhancement may occur in a suitable solvent, such as hexane, 2-propanol, 1-butanol, THF, methanol, ethanol, bovine serum albumin (BSA) and ethanolamine, to name a few exemplary solvents.

Figure 10A:
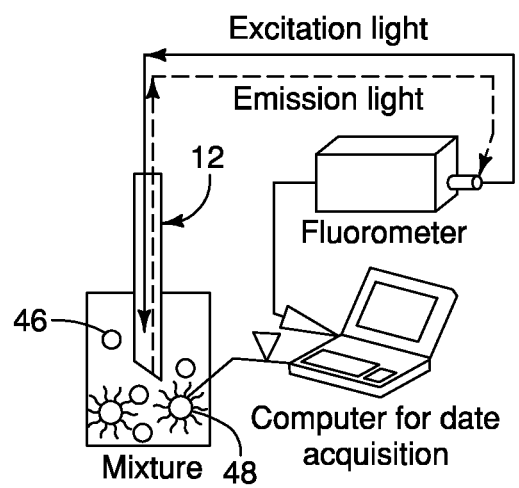
FIGS. 10A and 10B are schematic diagrams of fluorescence measurement of free fluorophores in solution using a tip of a quartz fiber polished at 45° (FIG. 10A) and PC biosensing both with and without NGP-SAMs (FIG. 10B)
Figure 10B:
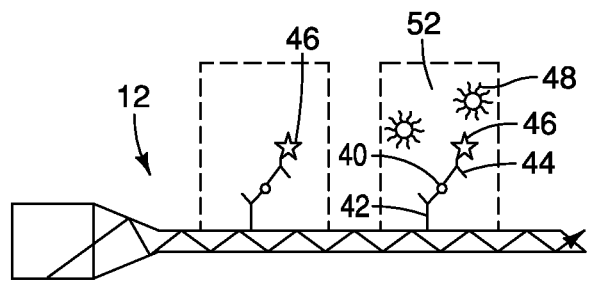
Figure 11A:
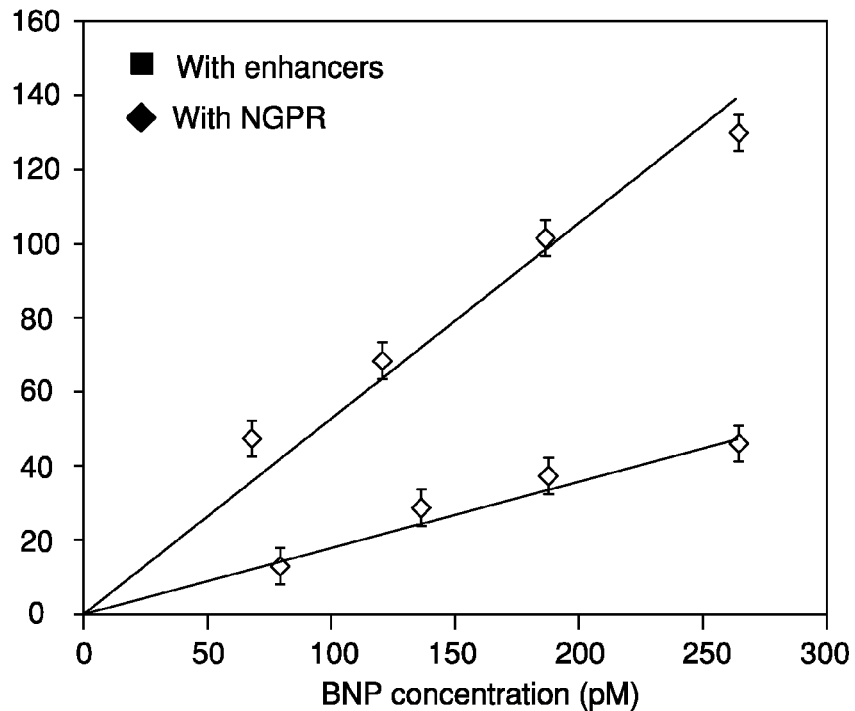
FIGS. 11A-11D are graphs respectively illustrating the NGPR effect on the biosensing of BNP, cTnI, MG, and CRP.
Figure 11B:
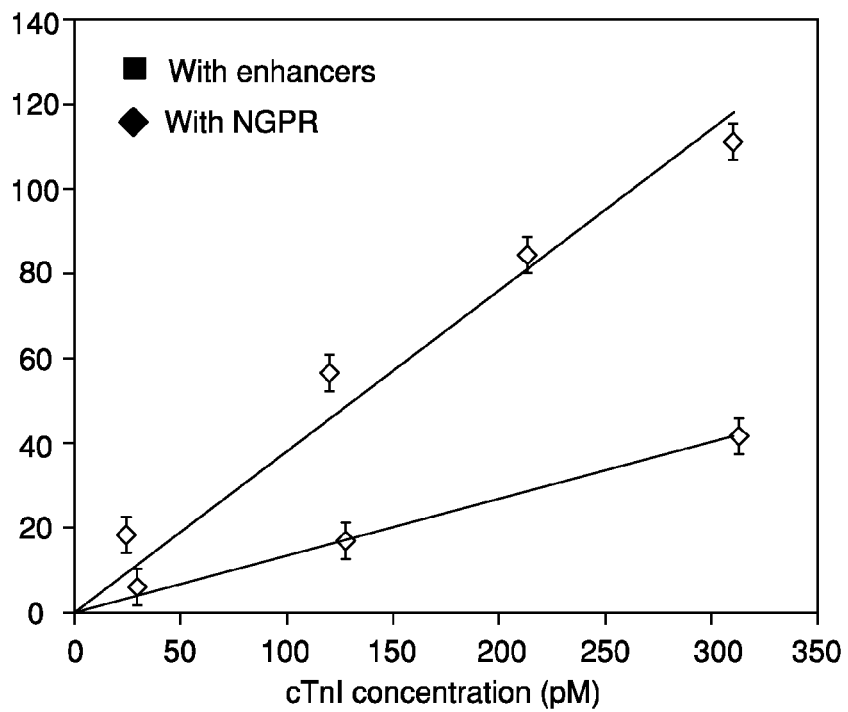
Figure 11C:
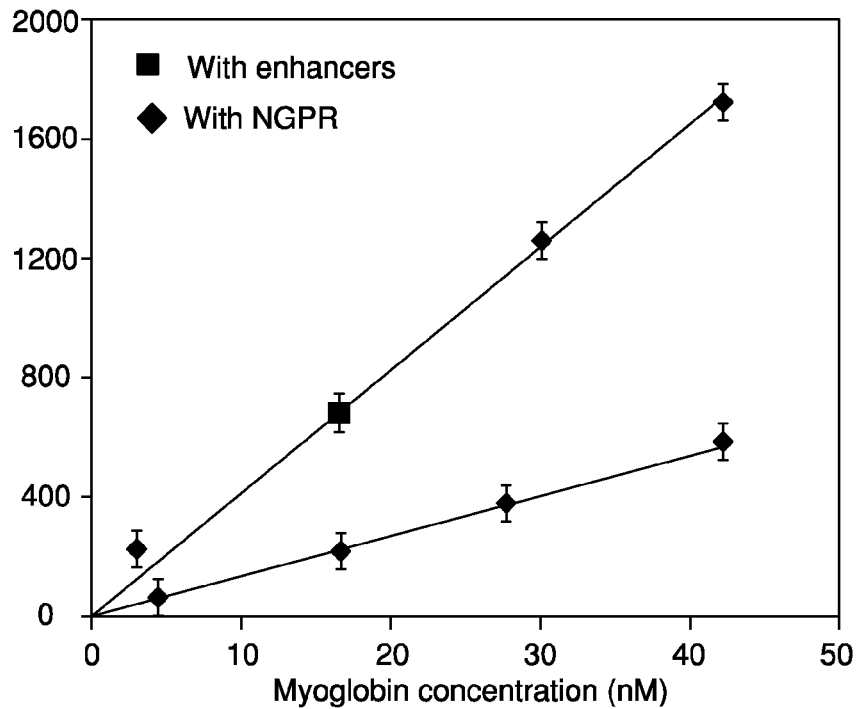
Figure 11D:
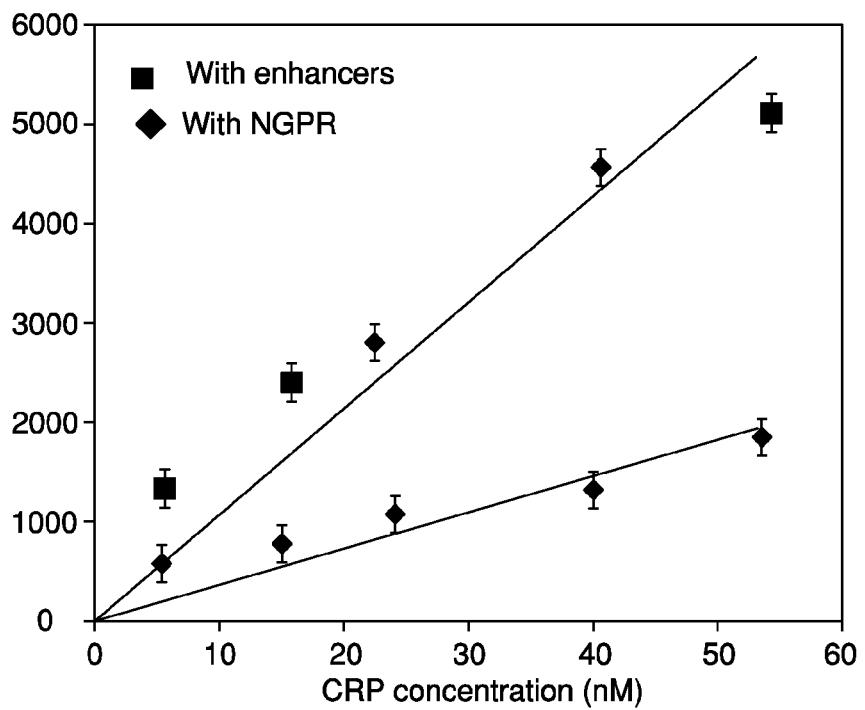

Turning to FIGS. 10A and 10B, other preferred embodiments of the invention include maximizing the signal enhancement by either providing nanogold particle 48 with SAMs 52 (NGP-SAMs), or combining the NGP-SAMs with a solvent 54 to form nanometal particle reagents (NMPRs), such that the nanogold particles of the NMPRs are placed at an optimal distance from the fluorophore 46 of the fluorophore-tagged 2° Mab 39. The enhancement level is cumulative of the portion by the nanogold particle 48 and that by the solvent 54.

FIG. 10A illustrates one of the optical sensing fibers 12 immersed in a solution, where the solution includes one of the solvents 54 having nanogold particles 48 with SAMs 52 disposed therein. Free fluorophores 46 are thereby kept at a predetermined distance from the nanogold particles 48, optimizing fluorescence of the fluorophore. The presence of the solvent 54 enhances fluorescence as well.

FIG. 10B illustrates one of the optical sensing fibers 12 (a) without nanogold particles 48 having SAMs 52 associated therewith, and (b) enhanced fluorescence of the fluorophore 46 surrounded by nanogold particles having SAMs.

One exemplary embodiment demonstrates the principle. 5 nmNGP-SAM2 nm are placed in ethanol, an effective NMPR previously tested for the protein C (PC) optical sensing fiber. FIGS. 11A-11D show that the NMPR can improve the sensitivity of all four individual cardiac marker sensors (by 1.5~3 times). Also, the enhancement level for the cardiac marker sensors by NGPR was even greater than the sum of the individual effects by the NGP and by the solvent. Preferably, the NMPR used does not interfere with biosensor reusability.

While it is contemplated that various nanometal particles and corresponding NMPRs may be used with the invention, nanogold and nanosilver particles will be shown and described for exemplary purposes.

Figure 8B:
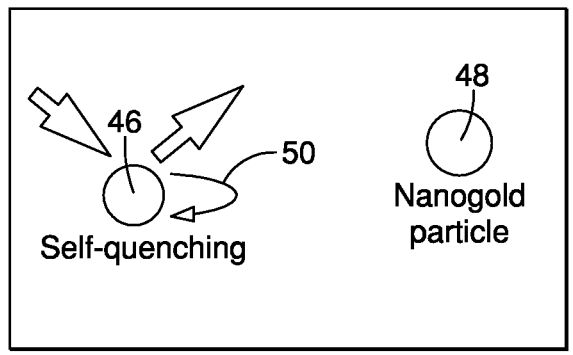
Figure 8C:
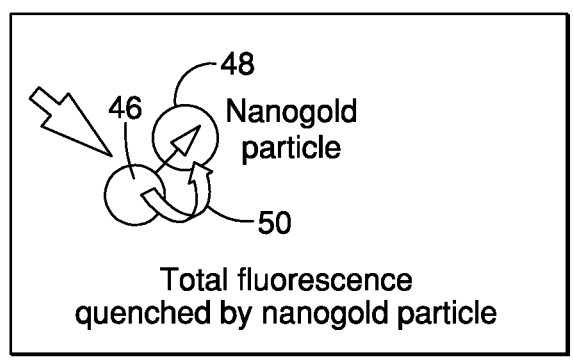

Generally speaking, as illustrated in FIGS. 8A-8C, when the fluorophore 46 is excited by photons, the fluorescence is usually emitted with a quantum yield (QY) lower than 1, mainly because of self-quenching. A nanogold particle 48 at an appropriate distance from the fluorophore 46 can reroute the electrons (represented by arrow 50) that are normally used for self-quenching, by absorbing these electrons in its strong plasmon field. Therefore, the QY of the fluorophore 46 can be artificially increased by the nanogold particle 48. The rerouting capacity of the nanogold particle 48 depends not only on the distance between the nangold particle and the fluorophore 46, but also the nanogold particle size because the plasmon field strength differs by the size. To adjust the distance between a fluorophore 46 and a nanogold particle 48, the self-assembled monolayers (SAMs) 52 having particular thicknesses were reacted onto the nanogold particle surface to obtain NGP-SAMs.

The effects of the distance between the nanogold particle 48 and the fluorophore 46 and the nanogold particle size on the fluorescence enhancement were investigated in free fluorophore solution (FIG. 10A) and also for the fiber-optic immuno-biosensing (FIG. 10B). The free form measurement was performed using a quartz fiber tip, while the immuno-sensing was conducted in a model system, protein C (PC; sensing range, 4-40 nM) biosensor. The concentration ranges of the NGP-SAMs and the fluorophore 46 in the samples were $10^{-8}$~$10^{-7}$ and $10^{-10}$~$10^{-7}$ M, respectively. The enhancement is defined as the increase in the fluorescence divided by the control fluorescence.

Figure 12A:
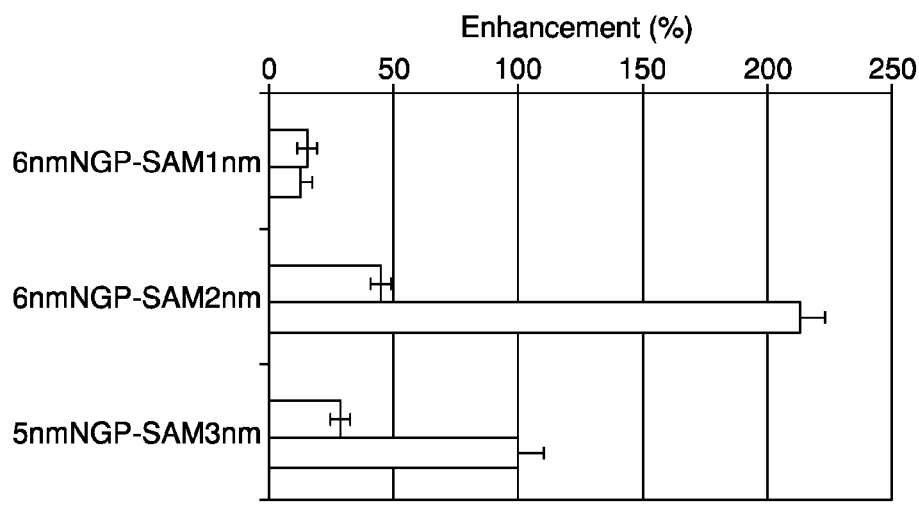
FIGS. 12A and 12B are graphs illustrating the effect of SAM thickness and the NGP size on fluorescence enhancement for free Cyanine 5 (CY5™) and in Cyanine 5 (CY5™) mediated PC sensing.

FIG. 12A shows the effect of the SAM 52 thickness, i.e., distance from the fluorophore 46, on the fluorescence enhancement for 5 nm nanogold particles 48 linked with 1, 2 and 3 nm SAMs. All three SAM 52 thicknesses show the enhancements for both free fluorophore 46 and the PC sensing. Among the three thicknesses SAMs 52 linked to 5 nm nanogold particles, a 2 nm SAM provided the highest enhancement (44 and 215%, free form and PC sensing, respectively). The SAM 52 having a thickness of 1 nm appeared to be too close to attract the electrons used only for self-quenching, while 3 nm, too far for effective electron rerouting.

Figure 12B:
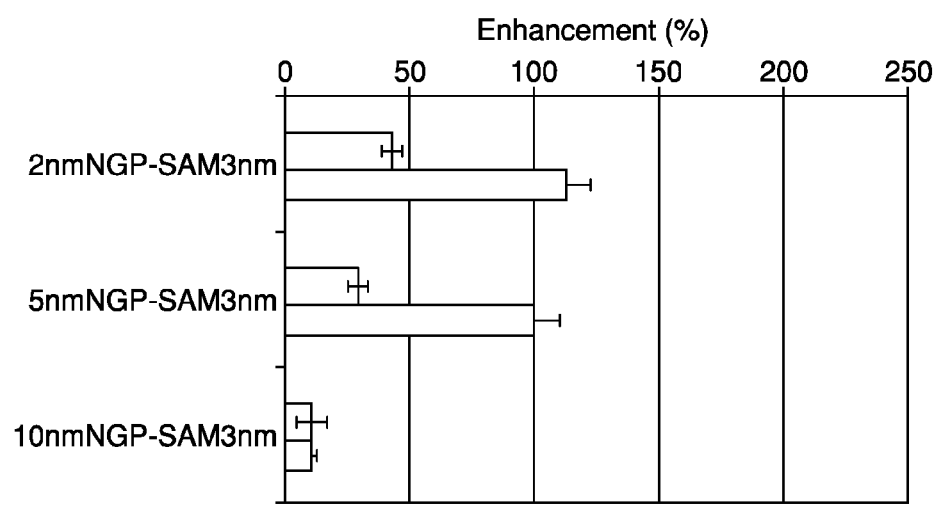

The effect of the nanogold particle 48 size (2, 5, 10 nm) was also investigated at a constant SAM thickness of (3 nm; FIG. 12B). The enhancements decrease as the nanogold particle 48 size increases, probably due to the different plasmon density for differently sized nanogold particles. The enhancement levels in PC sensing are much higher than that in free fluorophore 46.

While the size of the nanogold particles 48 and the thickness of the SAMs 52 may vary to suit individual applications, the preferred embodiment includes a 5 nm nanogold particle linked with 2 nm SAMs (5 nmNGP-SAM2 nm), which is optimized to enhance fluorescence with the enhancements of 44% and 215%, for the free fluorophore 46 and the PC sensing, respectively.

Figure 13A:
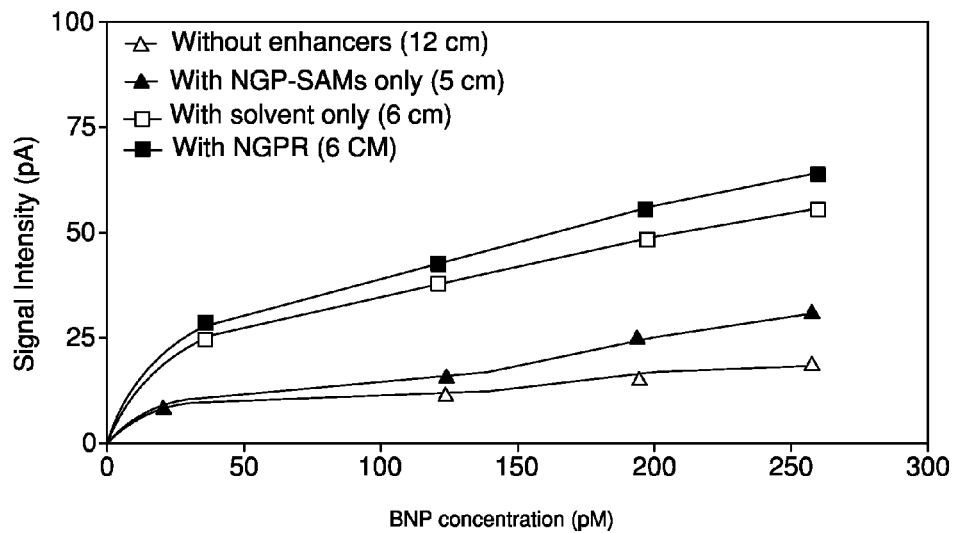
FIGS. 13A and 13B are graphs respectively illustrating the biosensing of BNP and cTnI without enhancers using 12 cm sensors with 10/10 minute incubations and with various enhancers using 6 cm sensors with 5/5 minute incubations.
Figure 13B:
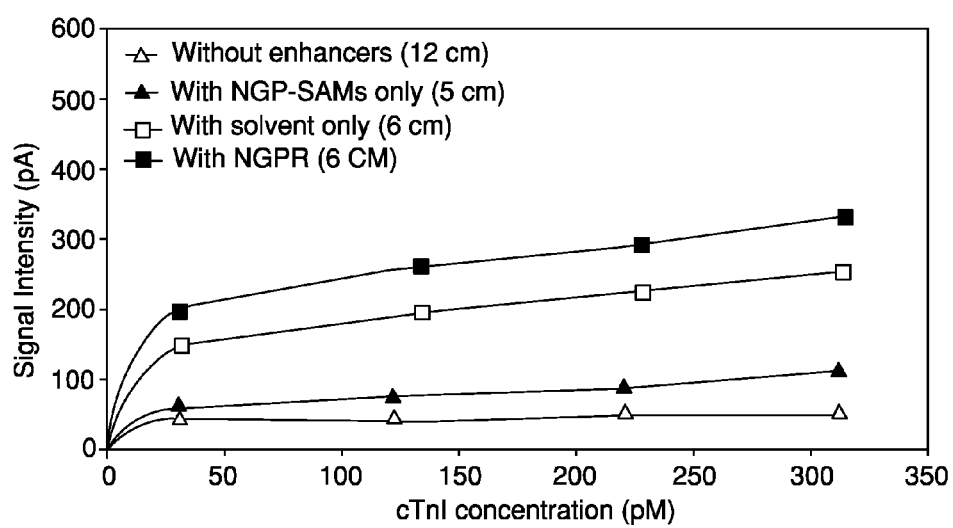

FIGS. 13A and 13B demonstrate that various solvents may be included to enhance fluorescence of the fluorophore 46. In one exemplary embodiment, enhancement is optimized with the 5 nmNGP-SAM2 nm that is mixed with the solvent to produce the nanogold particle reagent (NGPR), and tested for the 6 cm BNP and cTnI sensors. The fluorescence signal intensities were increased by 123~200% and 350~450% for BNP and cTnI biosensing, respectively (□). The enhancements by the NGPR appeared to be the additive of the enhancing by the NGP-SAMs and by the solvent. FIGS. 6a and 6b confirm that the optical sensing fibers with even a half length and a half assay time can provide sufficient sensitivity with these enhancers.

Figure 14:
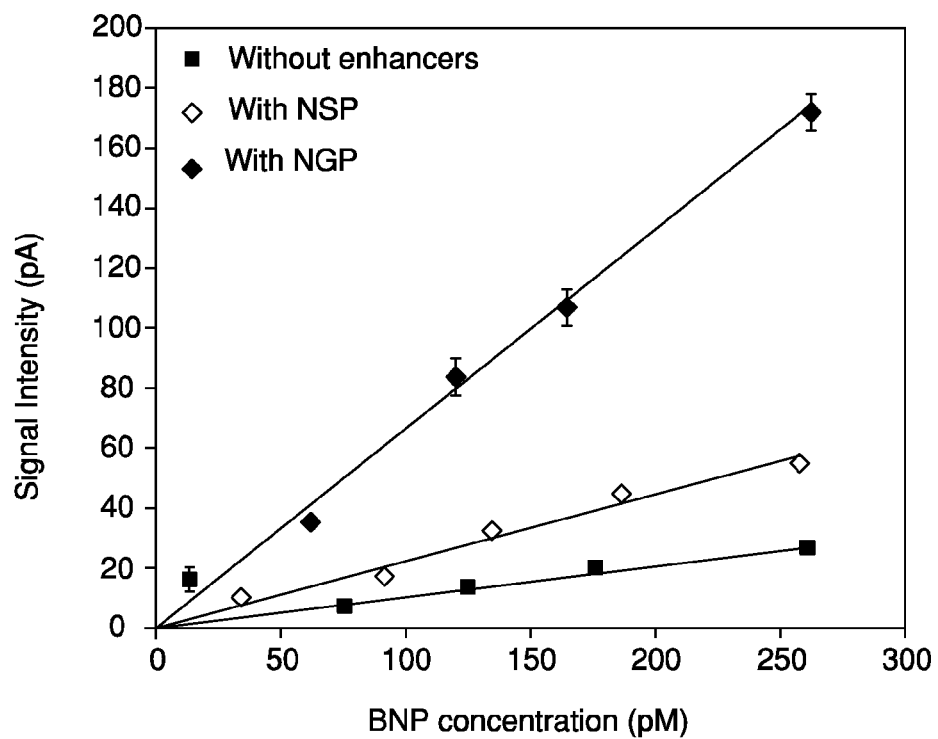
FIG. 14 is a graph illustrating fluorescence enhancement in BNP biosensing by ethanol and 1-butanol.

To select the optimal solvent for biosensing, various solvents, i.e., hexane, 2-propanol, 1-butanol, THF, methanol, ethanol, DMSO, and PBS buffer, were tested with the BNP sensing optical sensing fiber. Among the solvents, 1-butanol presented the highest enhancement i.e., showing a signal of 8 times of PBS buffer. FIG. 14 shows the performance of a BNP sensor using 1-butanol and ethanol as enhancers. By 1-butanol, the sensitivity of the BNP sensor increased by 5~7 times, 4~6 times higher than that of ethanol. Also, neither of these solvents negatively affected the reusability of the sensors.

Figure 15A:
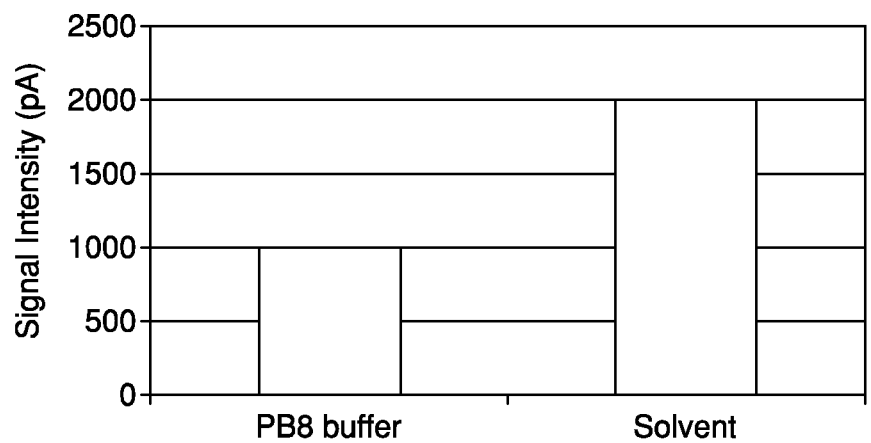
FIGS. 15A and 15B are graphs respectively illustrating the solvent effect on fluorescence enhancement for free Cyanine 5 (CY5™) and in Cyanine 5 (CY5™) mediated PC sensing.
Figure 15B:
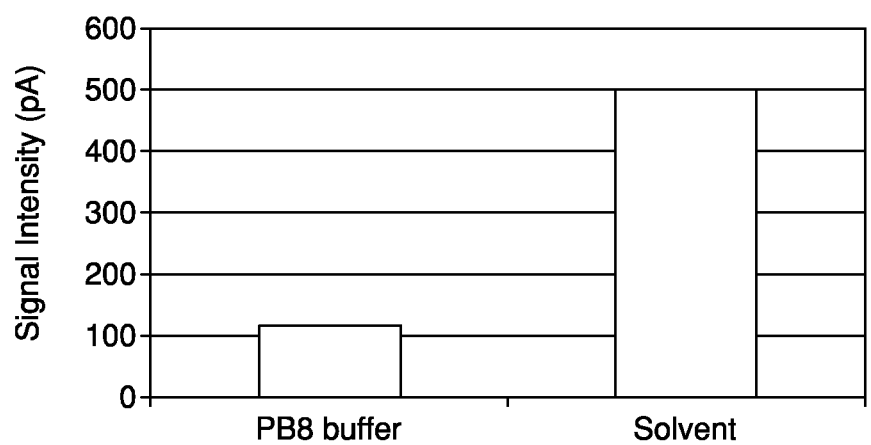

In one experiment, the fluorescence of free Cyanine 5 (CY5™) was measured in the phosphate buffered saline (PBS) buffer and also a biocompatible solvent (FIGS. 15A and 15B). The fluorescence signals in the solvent were doubled (FIG. 15a) for the free Cyanine 5 (CY5™), and in the PC sensing, four times of enhancement was obtained (FIG. 15B). The difference in enhancement is likely attributable to the difference between the freely floating fluorophore and surface bound fluorophore. For the fluorophore mediated immuno-sensing, Cyanine 5 (CY5™) was immobilized on the sensor surface by the sandwich protein complex. Therefore, the conformation change of the proteins in the solvent may also affect the light retrieval and fluorescence signal.

Figure 16:
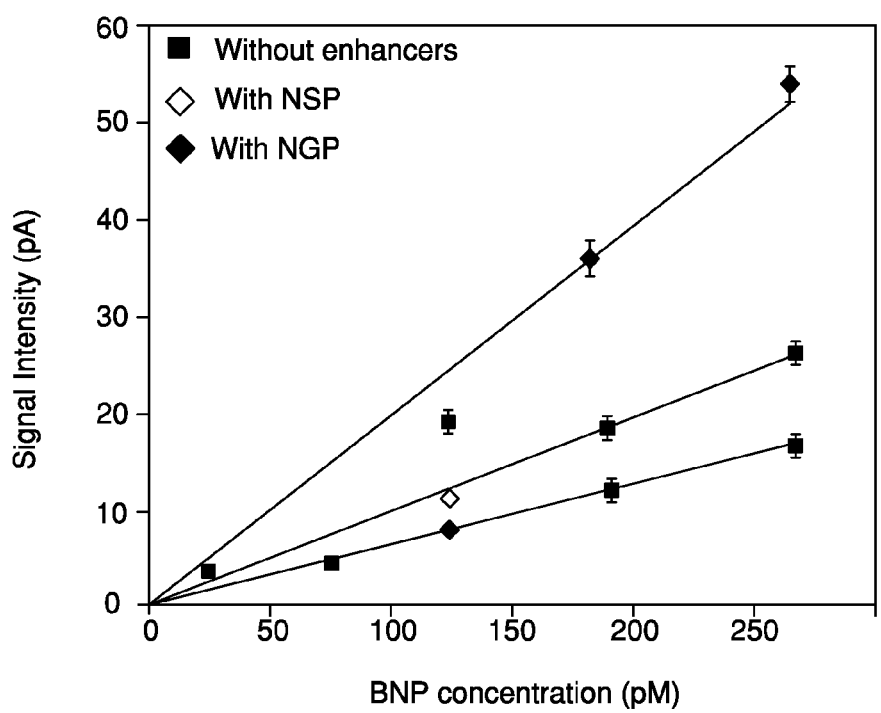
FIG. 16 is a graph illustrating fluorescence enhancement in BNP biosensing by 20 nmNSP-SAM3 nm and 20 nmNGP-SAM3 nm.

Nanosilver particles and NMPRs with nanosilver particles may be used to enhance fluorescence emission as well. For example, FIG. 16 illustrates fluorescence enhancement using 3 nm SAMs linked 20 nm nanosilver particles. Using a 1.5 cm BNP optical sensing fiber, the sensor provided very low signals (<30 pA; FIG. 16, ■) without enhancement. By using the nanosilver particles, 30%~35% enhancement was obtained (FIG. 1, ◊). Nanogold particles at the same size with same surfactant are also shown in FIG. 1, with 81%~138% enhancement (FIG. 16, ♦), still higher than that of nanosilver particles. Hence, nanogold particles were found to be more effective for the fluorescence enhancement than nanosilver particles, probably due to their higher electron affinity (2.3086 eV) than the nanosilver particles (1.3030 eV).

Self-Contained, Portable Sensing Devices

Embodiments of the invention contemplate a microfluidic "lab-on-a-chip" or microfluidic cartridge for use with biosensing applications where a plurality of microstructural components are integrated with one or more optical sensing fiber-based immunosensors.

Figure 17A:
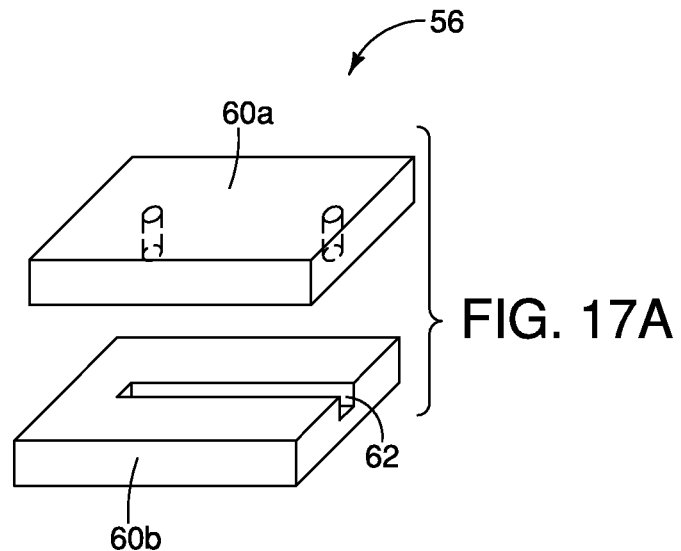
FIG. 17A is a side exploded view of a single channel biosensor according to another preferred embodiment of the invention.
Figure 17B:
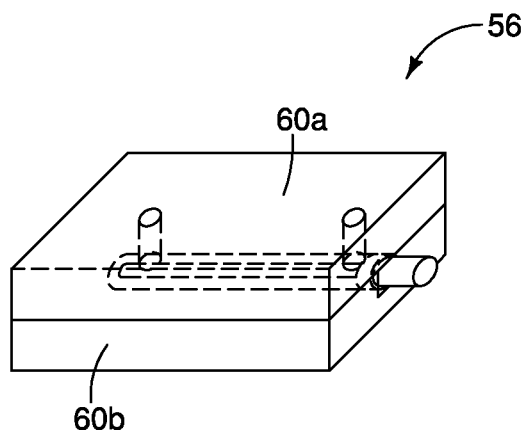
FIG. 17B is a side elevational view of the biosensor illustrated in FIG. 17A, shown with a fiber optic sensor disposed therein.
Figure 17C:
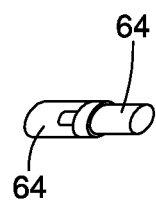
FIG. 17C is an enlarged perspective view of the fiber optic sensor illustrated in FIG. 17B.

An exemplary single biomarker biosensor is illustrated in FIGS. 17A through 17C, and is designated generally at 56. It should be noted that features of the single biomarker biosensor 56 may be expanded to include embodiments of a multiple channel biosensor.

The single biosensor 56 includes a plastic fluidic chip 60a, 60b having a single channel 62 disposed therein, and a dispenser that controls the exact of amount of fluid sample. In particular, FIG. 17B illustrates a fiber optic sensor 12 being coupled with the microfluidic chip 60a, 60b in a coupling arrangement that decreases or prevents leakage. The coupling includes hydrophobic/hydrophobic surfaces 64, because a gap through the hydrophobic/hydrophobic surfaces usually requires a high pressure drop to pass an aqueous liquid. With a gap of several μm at a coupling interface, pressure drops of several psi's can be tolerated by the hydrophobic/hydrophobic surface 64. This simple sealing method is significantly advantageous for coupling of various liquid containing parts, such as, biosensors incorporated with micro-fluidic lab-on-a-chip or the biosensor 56.

A hydrophobic patch (not shown) will preferably be fabricated over the surface at the end of a micro-channel and also the same patch should be fabricated over the surface at the coupling area of the optical sensing fiber.

The fully integrated optical sensing fiber-based biosensor 56 preferably includes a well-defined microfluidic channel 62 to promote advantages such as the high sensitivity and specificity over the other biological molecule recognition methods like electrophoretic separation or mass spectroscopy techniques. In order to make the microfluidic channel 62 suitable for the biosensor 56, high aspect ratio microchannels are preferred.

To obtain a high aspect ratio microchannel 62, a preferred method includes completely filling a micro-mold cavity that corresponds to the microchannel by plastic microinjection molding. More particularly, a Rapid Thermal Processing (RTP) method is preferably employed to provide a high aspect ratio fill of a negative volume impression of the microchannel 62 by exposing the mold insert surface to an infrared radiation source. Microinjection molding is an optimal technique capable of precisely fabricating microstructures using polymers at a low cost and in a high volume. However, fabrication of plastic microstructures in a HAR (high aspect ratio) without compromising cycle time has been considered as one of the most difficult tasks to accomplish because of the difficulty in the injection fill-depth control at low molding block temperatures. A complete fill of mold cavity with a HAR is almost impossible to achieve without sufficiently increasing the molding block temperature, to successfully flow the polymer inside the mold cavity. Also, before demolding, both the injection molded part and the molding block must be cooled down to the demolding temperature. This will lead to a huge increase in cycle time because the mold has to undergo heating and cooling cycles, whenever a plastic part is made.

Figure 18:
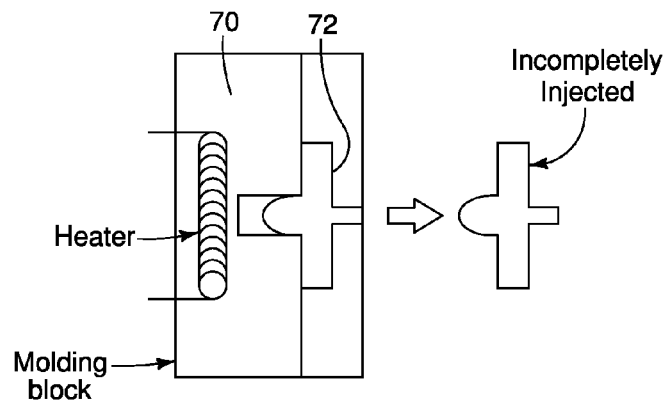
FIG. 18 is a schematic diagram of an incompletely injected polymer part due to premature cooling inside of a mold cavity.
Figures 19A, 19B, 19C, 19D:
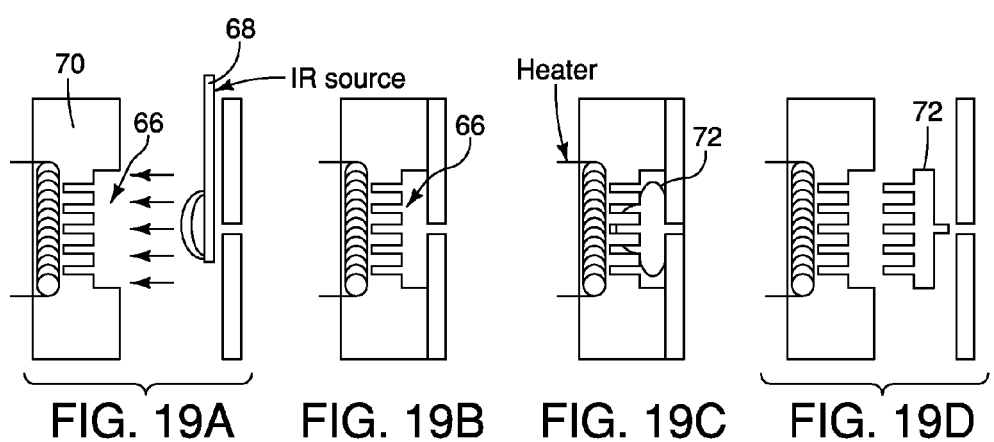
FIGS. 19A-19D are schematic diagrams illustrating injection molding of a biosensor housing having microchannels disposed therein using a rapid thermal process according to an embodiment of the invention.
Figure 20:
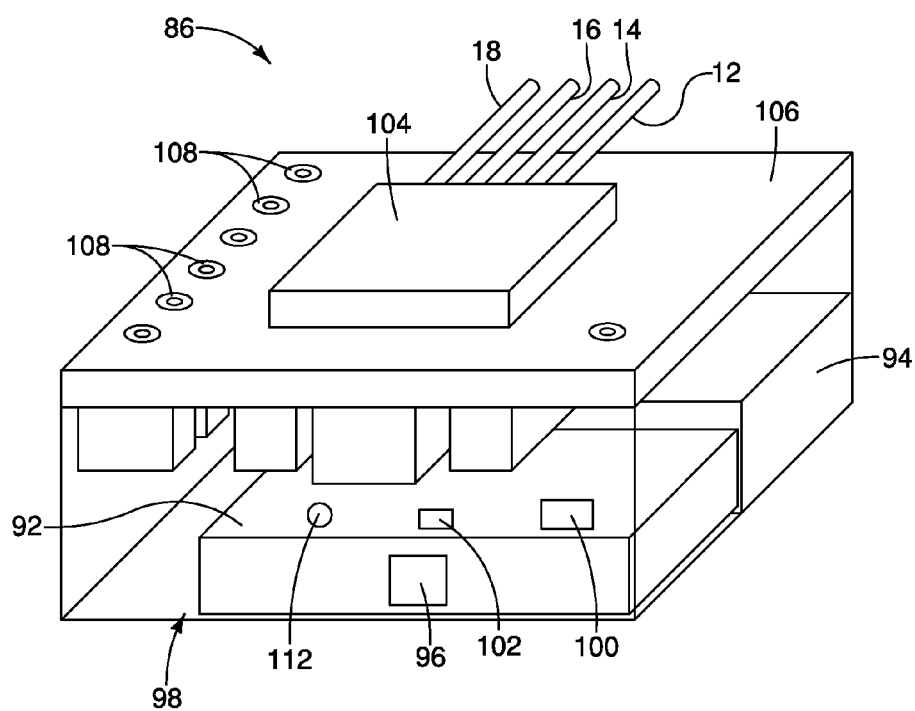
FIG. 20 is a front perspective view of multiple biomarker biosensor according to yet another embodiment of the invention.

FIGS. 18 and 19 illustrate a preferred embodiment that includes formation of high aspect ratio microchannels using a Rapid Thermal Processing (RTP) injection molding method, which is a preferred method of fabrication of devices such as the biosensor 10 illustrated in FIG. 1. In the injection molding method, a high aspect ratio mold fill is achieved by exposing a mold insert surface 66 to an infra red (IR) radiation heat source 68 to rapidly heat the surface of the mold insert higher than the tool temperature of the molding block 70. Most of the molding block 70, excepting an area-hear near the mold surface 66, can be maintained at a temperature less than glass transition temperature (demolding temperature). Since only a small section of the molding block 70 and the mold surface is heated to the glass transition temperature, an additional cooling system is not necessary and the cycle time is also reduced to about a minute for a typical plastic MEMS part.

In the preferred RTP injection molding method, the surface 66 of a Ni mold disk is heated with the IR radiation source 68, such as a high power halogen lamp. The radiation from the IR source 68 is focused to the surface of the Ni disk and, in a few seconds, the surface temperature of the replaceable Ni micromold disk reaches a temperature higher than the nozzle temperature. Then, the molding block 70 is closed and the molten plastic 72 is injected from the nozzle at high injection speeds. When the molten plastic 72 enters the mold cavity, it experiences an isothermal environment. The melt temperature and the Ni mold disk surface temperature will be the same at the instant when the plastic 72 is injected. Thus, there will be no heat transfer taking place inside the cavity for a very small period of time, and the surface heat of the Ni mold disk will help the plastic to be in a state of low viscosity. As a result, complete filling of the mold disk cavity can be achieved without any considerable increase in the cycle time for the operation of the injection mold machine.

Fabrication of devices of the invention can be conducted quickly and economically with the preferred RTP injection molding process. Fabrication of devices of the invention, such as the FIG. 1, FIG. 17A or FIG. 17B devices, can also be aided by low temperature bonding techniques including, for example, UV curable adhesion, self diffusion chain migration through mechanochemical polishing, and dielectric diffusion bonding of each layer to other layers.

Turning now to FIGS. 20-25 another preferred multiple biomarker biosensing module, generally at 86, will be shown and described. While it is contemplated that the sensing methods and optical sensing fibers 12, 14, 16, 18 of the invention may be configured to suit individual applications, one exemplary sensing device includes four optical sensing fibers 12, 14, 16, 18.

The preferred microfluidic biosensing module 86, is a real-time, automated, fluorophore-mediated, multi-cardiac biomarker sensing device that preferably includes a NMPR in addition to employing convective flow of the sample and the NMPR over the optical sensing fibers. Advantageously, the microfluidic biosensing module 86 may be provided as an automatic device for bed side, real-time heart attack diagnosis and prognosis.

Generally, in the microfluidic biosensing module, the four single-cardiac marker optical sensing fibers 12, 14, 16, 18 are connected in series to quantify four cardiac markers simultaneously. The sample and the reagents circulate at an optimal velocity in the microfluidic biosensing module 86 for effective mass transfer. The entire microfluidic biosensing module 86 is automatically controlled by a computer 87 having a computer program for user-friendliness and high consistency in the sensing performance. Importantly, the sensitivity of sensors is optimized by including a fluorescence enhancer.

More particularly, as illustrated in FIGS. 20 through 25, the microfluidic biosensing module 86 is a polymer fluidic module with a microchannel network 88, a plurality of micro valves 90a, 90b, 90c, 90d and at least one pump 36. Drive circuits 94 are also provided, as is a DAQ card 92 with an interface 96, such as a USB interface. These components of the module 86 are disposed within a housing 98 having dimensions configured to suit individual applications. In the exemplary embodiment, the housing 98 is approximately 15 cm in length, 12 cm in width, and 5 cm in height. Software is preferably provided to control flow operation through the microfluidic biosensing module 86, such as LabVIEW™. An activation switch 100 and an LED indicator 102 may also be provided.

A preferably disposable sensing biochip 104 is provided with the plurality of optical sensing fibers 12, 14, 16, 18, for example four, fluidly coupled with the biochip and disposed at least partially within corresponding microchannels 105 (FIG. 25) disposed within the biochip. The sensing biochip 104 is coupled to a reservoir plate 106, where the reservoir plate is preferably configured to be easily attachable and detachable from one or more reagent inlets 108 and waste outlets 110 via rubber sockets.

The microfluidic biosensing module 86 further preferably includes a 12 V DC power adapter 112, the activation switch 100 and LED indicator 102.

In this embodiment, a sample is loaded into the disposable polymer biochip 104 having the four microchannels 105. While the sample is circulated and incubated through the microchannels 105, the target proteins are reacted with the immobilized 1° Mabs on the surfaces of four optical sensing fibers 12, 14, 16, 18. The same incubation procedure will be used for the binding the fluorophore tagged 2° Mabs. The, the biochip 104 will be washed by flowing buffer solution after each incubation. The optical signal from the tagged fluorophore is picked up by an optical sensing fiber 12, 14, 16, 18 and measured by the fluorometer 42, such as the Analyte2000™ system. By immobilizing different types of antibodies in each of the optical sensing fibers 12, 14, 16, 18, the four-target assays will be achieved.

Figure 21:
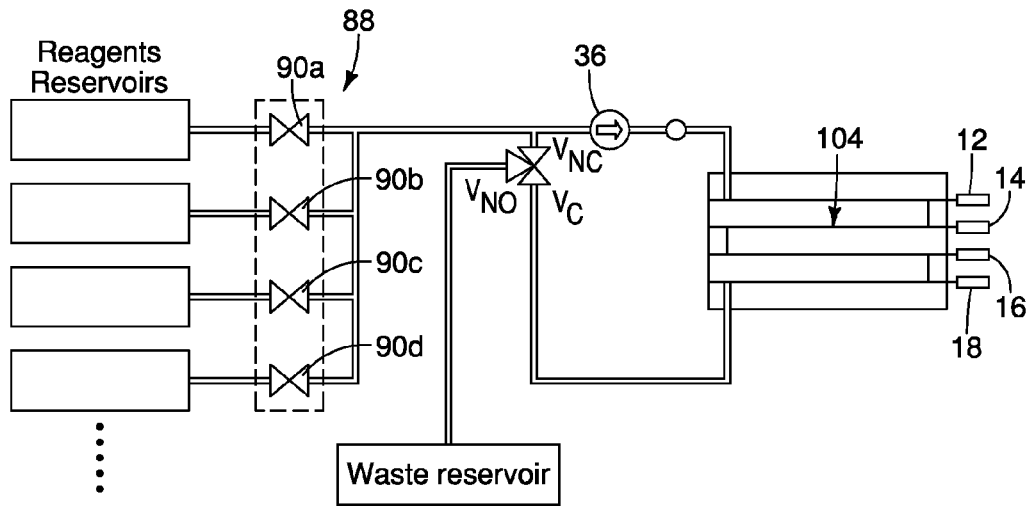
FIG. 21 is a fluid diagram of FIG. 22.

A schematic diagram of the automatic flow is shown in FIG. 21. One exemplary operation sequence is summarized as follows. A plurality of reagent reagent reservoirs 113a are fluidly coupled to the system, as is a waste reservoir 113b. 1) Sample or reagents loading, where one of a plurality of two-way valves 90a, 90b, 90c, 90d is open, the pump 36 is on, and valves $V_C$ and $V_{NO}$ are open. 2) During sample circulation and incubation, all of the two-way valves 90a, 90b, 90c, 90d are closed, the pump 36 is on, and valves $V_C$ and $V_{NC}$ are open. 3) During wasting and washing, the two-way valve 90a, 90b, 90c, 90d opening to a reservoir of washing buffer is open, the pump 36 is on, and valves $V_C$ and $V_{NO}$ are open.

Figure 22:
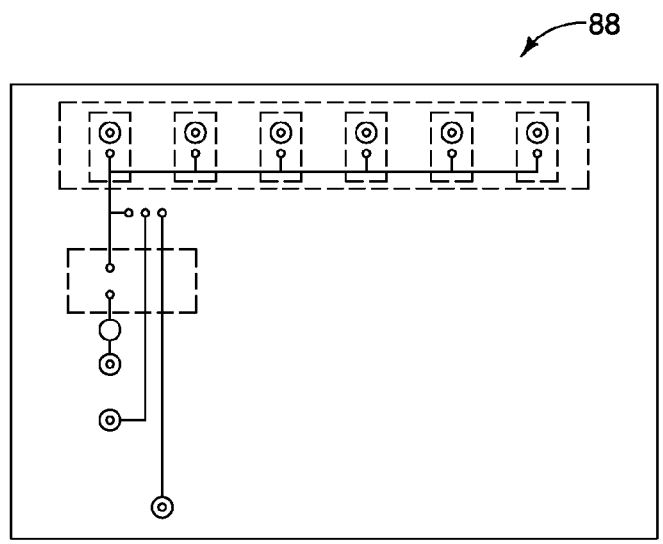
FIG. 22 is an alternate view of the fluid diagram of FIG. 23 shown with a reservoir plate of the biosensor of FIG. 22.

FIG. 22 illustrates the microchannel network 88, where the active valves 90a, 90b, 90c, 90d and pumps 36 are mounted on the microfluidic biosensing module 86 and connected by the microchannel network inside of housing 98 of the microfluidic biosensing module.

Figure 23:
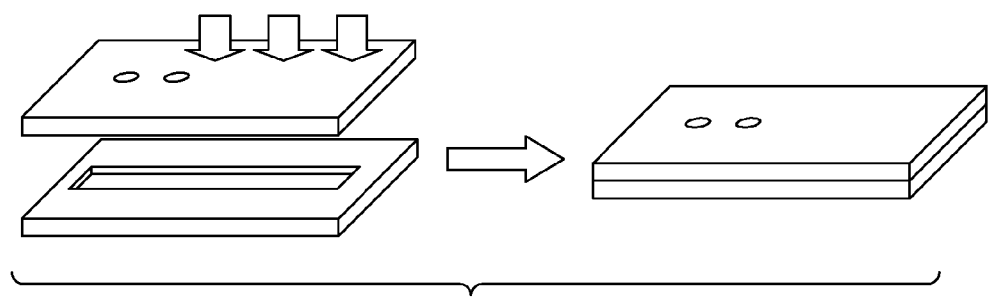
FIG. 23 is a schematic diagram illustrating an exemplary method of fabrication of the polymer microfluidic biosensor of FIG. 22 via micromachining and thermal bonding techniques.

FIG. 23 illustrates an exemplary method of fabrication of the polymer microfluidic biosensing module 86 via micromachining and thermal bonding techniques.

Figure 24A:
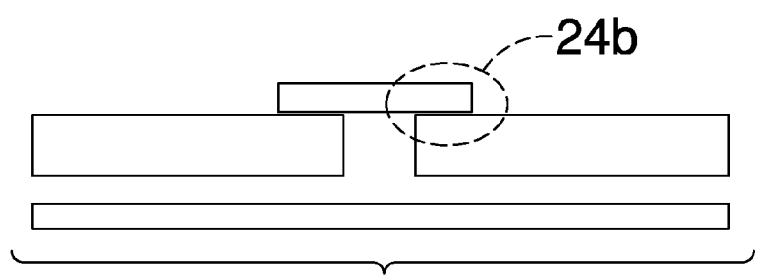
FIGS. 24A and 24B are a schematic diagram illustrating a bubble trap between a pump and a biochip of a microchannel network of the module illustrated in FIG. 22.
Figure 24B:
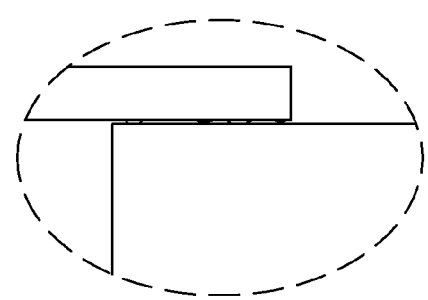

Advantageously, the microfluidic biosensing module 86 includes a bubble trap 114 between the pump 36 and biochip 104 to remove bubbles in the microchannel network 88, as illustrated in FIG. 24. A hydrophobic gap between the rough surface of a Teflon cover 115 and microchannel network 88 is several μm thick, which will not permit liquid to pass but permits the air to pass.

Figure 25:
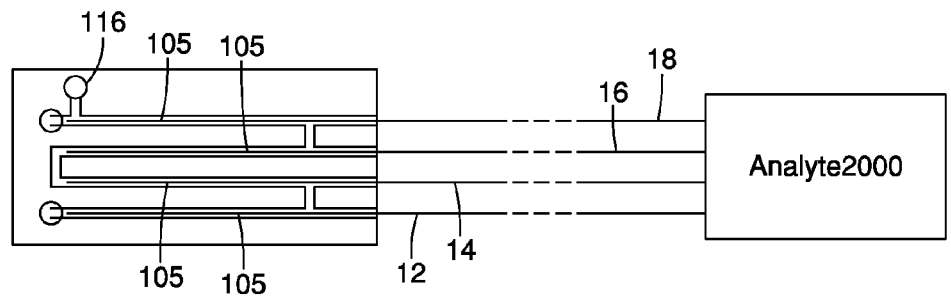
FIG. 25 is a schematic diagram of the biosensor illustrated in FIG. 22.

FIG. 25 illustrates a schematic diagram of the disposable polymer biochip 104 with the four microchannels 105 and optical sensing fibers 12, 14, 16, 18. The four microchannels 105 are connected to each other serially in the biochip 104. Each microchannel 105 is coupled with a respective one of the optical sensing fibers 12, 14, 16, 18, on which optical sensing fiber is immobilized one type of specific antibody, or 1° Mab. For minimizing the sample and cross contamination, there is a self-sealing sample loading pad 116 near the inlet 108 of the biochip 104 to load the sample by using a syringe. The self sealing is fabricated with PDMS. After pulling off the needle of a syringe, it will be self-sealed due to the mechanical property of PDMS.

Figure 26:
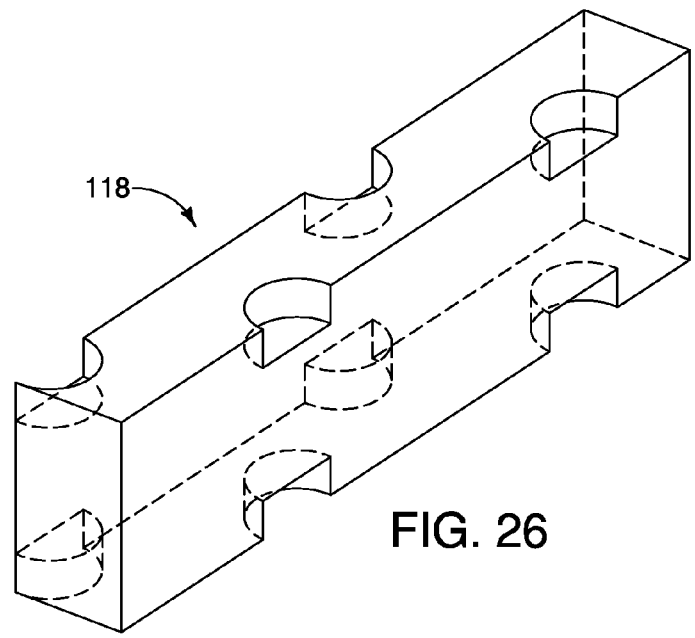
FIG. 26 is a front perspective view of serpentine bump structure inside of the microchannel of FIG. 22.
Figure 27A:
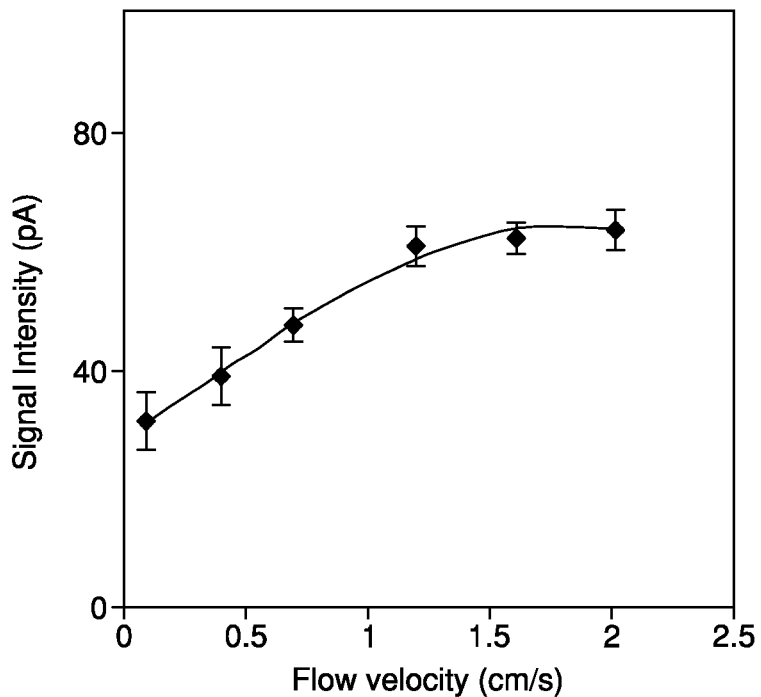
FIGS. 27a-27d are graphs illustrating the various effects on the BNP sensor, including (a) effect of flow velocity, (b) effect of the sample, (c) effect of the reagent incubation time, and (d) the standard curve for BNP.
Figure 27B:
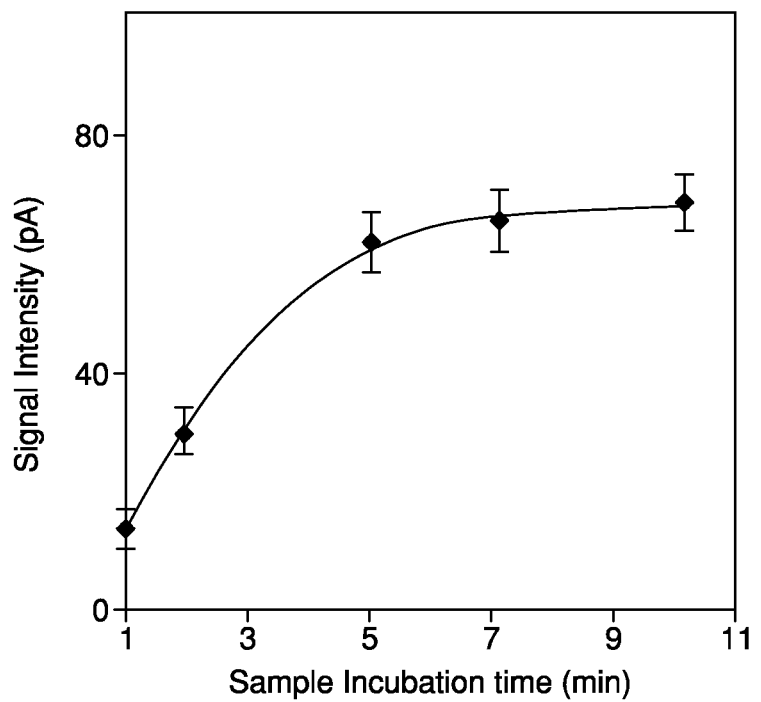
Figure 27C:
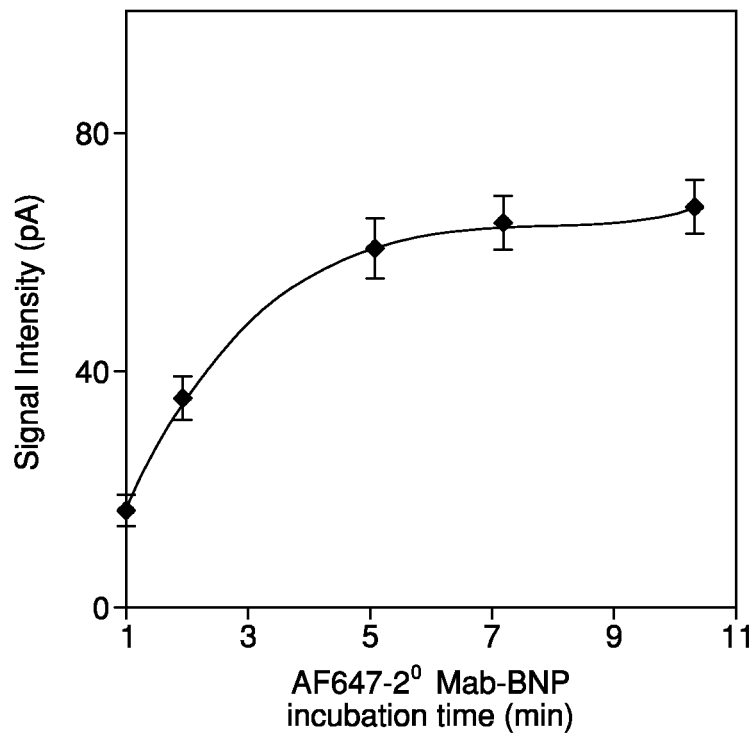
Figure 27D:
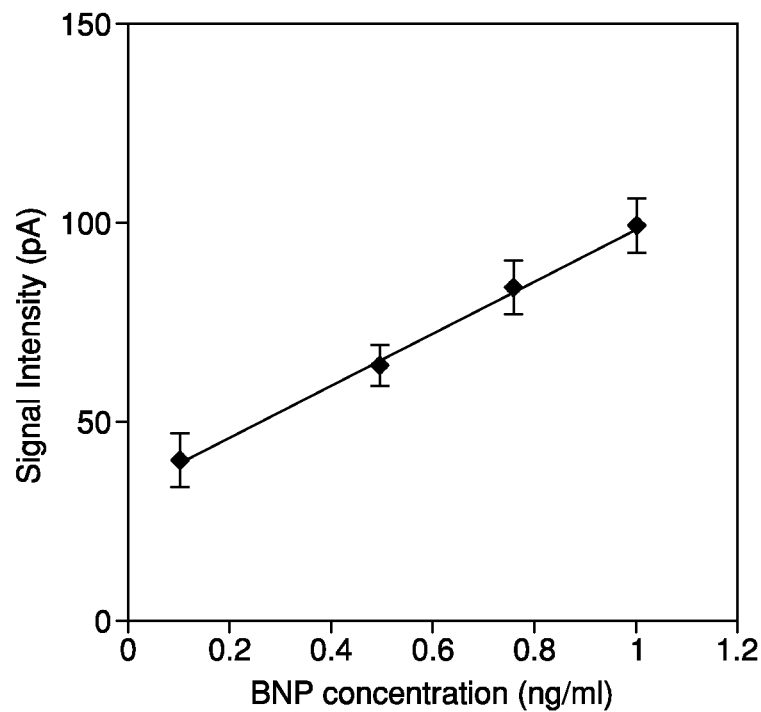

As illustrated in FIG. 26, in order to enhance the molecular binding efficiency at the microchannel 105, a serpentine bump structure 118 inside of the microchannel is included in the sensing biochip 104. Preferably, the serpentine bump structure 118 is disposed at top and bottom surfaces of each of the microchannels 105. As compared with the flat inner surface, the serpentine bump structure 118 greatly improves the molecular transport to the optical sensing fibers 12, 14, 16, 18 to enhance sensing performance.

Additional Methods and Experimental Results

Purified cTnI, MG, and CRP from human heart and respective murine, monoclonal antibodies were obtained. Human BNP and two different murine, monoclonal anti-human BNP were obtained. Alexa Fluor 647 reactive dye (AF647; the maximum excitation and emission at 650 and 668 nm, respectively) and human serum albumin were obtained. Quartz optical fibers (600 μm core diameter) and Fluorometer, Analyte 2000™ were obtained.

To emulate MG-, BNP-, cTnI-, or CRP-free human plasma, samples were prepared in HSA solution at 103 mg/ml-phosphate buffered saline. The conjugation of AF647 with the respective second monoclonal antibody (AF647-2° Mab) was performed according to manufacturer's instructions. Tapered optical fibers (3-12 cm long) were chemically treated to immobilize the first monoclonal antibodies (1° Mabs), against MG, BNP, cTnI, or CRP, on the surface of respective fibers via avidin-biotin bridges. Then, the fibers were inserted into channels in the sensing chip and the ends were sealed. Assays with static incubation (no flow) were performed. For the assay with convective flow, the sample and the AF647-2° Mab were injected and circulated within an enclosed sensing unit at a pre-determined velocity for a pre-determined incubation period.

The target sensing ranges for BNP and cTnI are 0.1~1 ng/ml (26~260 pM) and 0.7~7 ng/ml (30~300 pM), respectively. One experiment was performed with 12 cm sensor and 10 minutes each for the sample and the AF647-2° Mabs incubation. With static incubation (i.e. no flow during the incubation), the signal intensity of the BNP and cTnI sensor was very low (data not shown). Convective flow can improve the sensor performance significantly by increasing the analyte mass transport to the sensor surface. The BNP sample at 0.5 ng/ml and AF647-2o Mab-BNP were circulated in the sensing system at a flow velocity between 0.1 and 2 cm/s during the reaction (incubation). In the range of 0.1 to 1.2 cm/s, as the velocity increases, the signal intensity rapidly increases approximately 10 times of that without flow. At velocities higher than 1.2 cm/s, the intensity increase becomes insignificant (2%), indicating that the reaction kinetics changes from the mass-transport-limited to the reaction-limited. Therefore, 1.2 cm/s was selected to be the flow velocity for our BNP sensing.

Figure 7D:
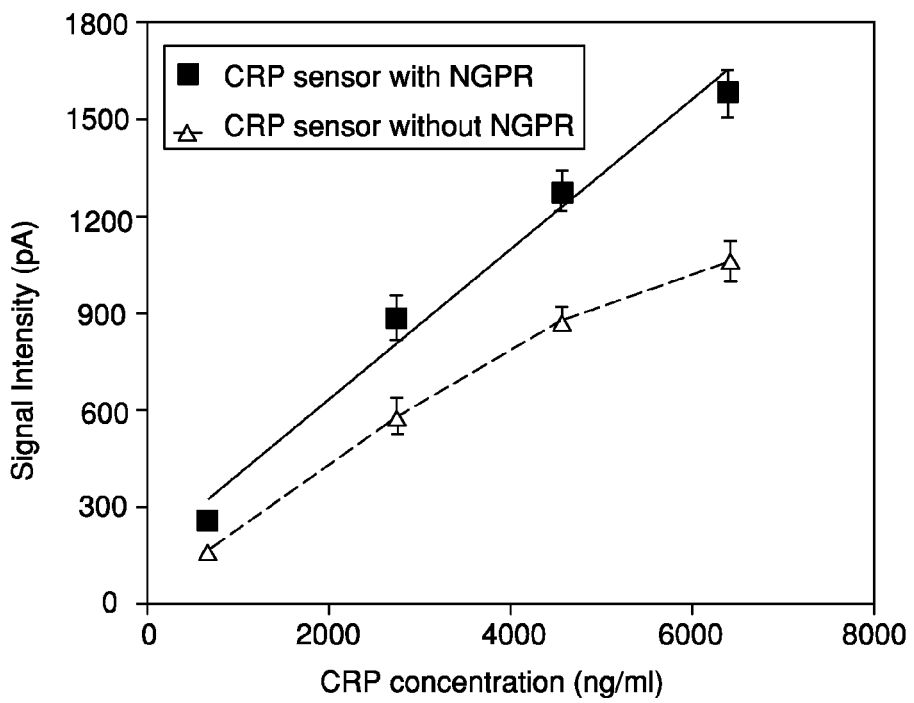

In the clinical practice, a short assay time is especially beneficial for rapid disease diagnosis. Therefore, a study was performed to minimize the assay time. The BNP sample (0.5 ng/ml) was incubated between 1 and 10 minutes while keeping the AF647-2o Mab-BNP incubation for 10 minutes, and vice versa. Results indicate that the molecular mass transport and the immuno-reaction on the sensor surface for both incubations may be completed in 5 minutes. Therefore, 10 minutes is probably sufficient for the sample and reagent incubations and one assay can be completed within 15 minutes including sample/reagent application and sensor regeneration. The sensitivity of the optimized BNP sensor was investigated in the target sensing range (FIG. 7D). The signal intensity is linear with the analyte concentration and the sensor clearly quantifies BNP concentration at an average signal-to-noise (S/N) ratio of 25.

Similarly, the signal intensity for the cTnI (3 ng/ml) rapidly increases with the increase in the flow velocity until the velocity reaches 1.2 cm/s. At this flow velocity, the incubation time optimization was also performed for the cTnI sensing and as for the BNP sensor, 15 minutes is sufficient for completing a cTnI assay (data not shown). The signal intensity is linear with the cTnI concentration, at an average S/N ratio of approximately 25.

The target sensing ranges for MG (70~700 ng/ml; 4~40 nM) and CRP (700~7000 ng/ml; 5.6~56 nM) are approximately 100 times higher than those of BNP and cTnI. Unlike the BNP and cTnI sensors, the convective flow did not improve the MG and CRP sensor performance significantly, because the analyte transport to the sensor surface is sufficient without convection. The effect of the sample and the AF647-2° Mabs incubation times on the MG and CRP sensor performance was also investigated. Measurements were performed at a flow velocity of 1.2 cm/s, because eventually, all four sensors including the BNP and cTnI sensors are placed in one sensing unit for multi-sensing. As expected, 5 minutes for each incubation period is more than sufficient for both the MG and CRP sensors. The signal intensities for the 12-cm MG and CRP sensors are much higher than those for the BNP and cTnI sensors. Therefore, a study was performed to reduce the sensor size to 3-cm to minimize the amount of the sample and reagents to be used. Compared to the 12-cm sensor, the signal intensities from the 3-cm sensors are about 40-50%, although the sensor size is reduced by 75%. The signal of the 3-cm MG and CRP sensors is also in a linear relationship with the respective MG and CRP concentration, at an average S/N ratio of approximately 50.

To investigate the possible cross-reactivity among the BNP, cTnI, MG, and CRP sensors, each sensor was tested to samples containing the other three analytes at their upper limit of sensing ranges. For example, for a BNP sensor, cTnI (7 ng/ml), MG (700 ng/ml), and CRP (7000 ng/ml) were tested and the fluorescence signals were compared to that of BNP measurement at the lower sensing limit (0.1 ng/ml). All four sensors demonstrated a very high specificity with little cross-reactivity when the other three analytes were present in the sample.

For the simultaneous quantification of these markers in a multi-sensing unit, after the sample incubation, each AF647-

2° Mab needs to be applied to the respective sensor. If the four different AF647-2° Mabs do not cross-react, for an easier design and operation of the sensing system, a mixture of the AF647-2° Mabs can be applied through the multi-sensing unit. The effect of the second antibody mixture on each sensor performance was studied.

The signal intensity is generated by a MG sensor using only AF647-2° Mab-MG or a mixture of four AF647-2° Mabs. The signal intensities generated by the mixture showed a slight signal reduction (<10%), with a similar standard deviation. For the BNP, cTnI, and CRP measurements using the antibody mixture, similar results were obtained (data not shown). A possible cause for the signal reduction could be that the presence of other types of molecule causes a slower mass transfer rate. Thus, the quantification of these cardiac markers with the mixed AF647-2° Mabs can be as accurate as that with the respective AF647-2° Mabs if the measurements are always performed with the antibody mixture. Therefore, a mixture of four different second antibodies may be used for simultaneous four markers quantification.

Thus, it is contemplated that embodiments of the invention would provide a fiber-optic biosensing system for the simultaneous quantification of four cardiac markers for rapid coronary disease diagnosis and prognosis. As a preliminary matter, four individual BNP, cTnI, MG, and CRP sensors were developed, though it is contemplated that the invention may encompass additional sensors for additional cardiac markers. The sensors showed excellent performance in quantifying these cardiac markers in their clinically significant ranges within 15 minutes, at a S/N ratio of 25-50. The cross-reactivity of the four sensors was also found to be negligible. A mixture of four AF647-2° Mabs has shown a minimal interference to the four sensors, indicating that the mixture can be applied through a multi-sensing unit for simultaneous detection with an easier operation.

The invention also contemplates simultaneous quantification of these four cardiac markers using a multi-sensing unit. A microfluidic system will be incorporated in the unit for precise fluid control. Micro-electro-mechanical systems (MEMS) technology will be utilized for the development of an automatic, smaller, and more cost-effective sensing chip.

Additional experimental results are summarized as follows.

With respect to the specificity of the biosensor, since blood contains a variety of proteins that are structurally similar to PC, the specificity of the biosensor was tested. PC samples (0, 1.25, or 2.5 µg/ml) were spiked with a physiological concentration of one of the homologues (Factor II, VII, IX, or X). As well, samples containing a mixture of all five proteins were prepared. Experimental results demonstrate the high degree of specificity of the biosensor.

One optimal 1° Mab immobilization method was determined as follows. Two methods for immobilizing the 1° Mab onto the fiber surface were explored. Direct binding involves directly linking the 1° Mab to the fiber surface via a crosslinker. The avidin-biotin method links biotinylated 1° Mab to avidin already immobilized on the fiber surface. As a test, a series of PC concentrations (0.31, 1.3, and 2.5 µg/ml in PBS) were assayed on fibers prepared with each method (FIG. 6). For all cases, fibers utilizing the avidin-biotin bridge demonstrated higher signal intensities when compared to direct binding fibers (in some cases, increases of over 350%).

Efficacy of blocking buffers were determined when fibers were blocked with 1 and 2 mg/ml BSA, and 0.1, 1.0, and 5.0 M ethanolamine. The background fluorescence was examined to determine the effectiveness of BSA and ethanolamine as blocking buffers. Fibers blocked with BSA gave high background fluorescence intensity of the control with high standard deviation (80-90% of control). Ethanolamine was more effective in reducing background noise, reducing the background to 10-20% of the control (FIG. 7).

The plasma effect was demonstrated by noting that the high viscosity of the plasma sample decreased the PC transport rate from bulk solution to fiber surface, which leads to signal intensity reduction of PC measurement at a limited reaction time. The signal intensity from PC measurement in plasma was decreased by 70% compared to pure buffered PC measurement.

The effect of convection on sensitivity enhancement was determined as follows. Due to the high viscosity of blood plasma, the diffusional mass transport rate of molecules from the sample to the sensor surface was found to be very slow. Therefore, the signal intensity, after a limited incubation time, is much lower for the plasma samples compared to the buffered samples. To enhance the sensitivity, another mechanism of mass transport, convection (flow), was added to the sensing system. The signal intensities at various flow velocities, when 1 µg/ml of PC samples in plasma was applied to the sensing chamber. When the sample velocity was 0.5 cm/sec, the signal intensity increased more than three times of the stagnant system.

To provide continuously convective mass transfer with the minimum sample volume, a unit was designed to circulate the liquid. For this system the optimum flow velocity was determined to be 0.7 cm/s. After this optimum circulation velocity was determined, a study was performed to minimize the assay time. The sample incubation for only 30 seconds provided 91% of the signal intensity of the 3 minutes. For the Cy5-2° Mab incubation study, the 2 minute incubation provided 91% of the signal intensity of the 3 minutes one. With the combined incubation times of 0.5 and 2 min for sample and Cy5-2° Mab, PC concentrations at 0.5~2.5 µg/ml were measured (FIG. 10). The sensor clearly differentiated PC amount in the range with an average standard deviation of 5%. Therefore, 0.5 and 2 min incubation times were selected for PC sensing, allowing completion of the entire PC assay within 5 minutes.

A preliminary study for cardiac troponin t (cTnT) sensing was conducted. Since the target sensing range of cTnT (1-3 ng/ml) was approximately 1000 times lower than that of PC (0.5-2.5 µg/ml), 12.5 cm sensor was used instead of 6 cm and the incubation times were extended to 10/10 minutes. The sample and Cy5-2° Mab were applied either with static incubation or convective flow at the flow rate of 0.3 ml/min during cTnT sample and the sensor was able to measure the cTnT level as low as 1 ng/ml without difficulties.

Antibody-antigen complexes are formed by several non-covalent interactions, such as electrostatic, Van der Waals, and hydrogen bonding. Most immunoaffinity regeneration processes with monoclonal antibodies require harsh elution conditions, such as high or low pH, and/or high ionic strength. Therefore, the effect of the extreme pH on the regeneration was considered.

A fiber regeneration step can elute PC molecules captured during the assay, from the fiber surface, with little damage to the 1° Mab. Without regeneration, after successive assays, the fiber surface becomes saturated with the immuno-complex (1° Mab/PC/Cy5-2° Mab). Without any regeneration step, 6 cm fiber can be reused approximately 2.5 times. Various regenerative buffers used in Protein C immuno-affinity chromatography were tested to elute the immuno-complex from the fiber surface. The test results showed that the metal free TEA buffer (0.1 M NaCl, pH 11.0) was found to be the most effective. With TEA buffer, the fiber reusability was extended up to 7 times.

A mathematical model for immuno-reaction between PC and anti-PC on the fiber surface was developed and solved by the finite difference method. To examine how the increased viscosity affects the overall binding kinetics, a computer simulation was performed to check the molecules' overall distribution in liquid phase. In plasma, there is much less reduction of PC concentration in the liquid phase due to the less transport to the fiber surface, and therefore, less reaction on the fiber surface. A theoretical analysis of mass transport by convection was performed using film theory. At higher flow velocity, the film thickness becomes thinner, and thus increasing the overall mass transport rate.

While various embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the following claims.

What is claimed is:

1. A biosensing method for simultaneously detecting and quantifying two or more target biomarkers, said method comprising:
   providing at least two optical waveguides, each of the at least two optical waveguides being disposed at least partially in a respective microfluidic channel of a serpentine shaped chamber, the at least two optical waveguides being fluidly coupled to one another in series within the serpentine shaped chamber;
   selecting 1° Mabs corresponding to each of the two or more target biomarkers;
   immobilizing the 1° Mabs on the optical waveguides;
   exposing to the 1° Mabs a sample believed to contain the target biomarkers using convective flow within the serpentine shaped chamber, wherein the sample flows through the serpentine shaped chamber and flows over each of the at least two optical waveguides in series;
   providing fluorophore-tagged 2° Mabs corresponding to the target biomarkers;
   exciting the at least two optical waveguides; and
   observing a fluorescence emission to determine the presence and quantity of the target biomarkers.

2. The method of claim 1 wherein said providing at least two optical waveguides comprises providing at least two quartz optical sensing fibers coupled to one another in series.

3. The method of claim 1 wherein said providing at least two optical waveguides comprises providing four optical sensing fibers coupled to one another in series.

4. The method of claim 3 further comprising providing four 1° Mabs corresponding respectively to Cardiac troponin I (cTnI), myoglobin (MG), B-type natriuretic peptide (BNP) and C-reactive protein (CCRP).

5. The method of claim 3 further comprising providing four 1° Mabs corresponding respectively to PC, PS, ATIII and PLG.

6. The method of claim 1 wherein said selecting 1° Mabs comprises selecting the 1° and 2° Mabs such that the 1° has lower affinity with respect to the target biomarker than does the 2° Mab.

7. The method of claim 1 wherein said providing at least two optical waveguides comprises providing at least two optical sensing fibers coupled to one another in series, and wherein said immobilizing the 1° Mabs on the optical waveguides comprises immobilizing the 1° Mab via an avidin-biotin bridge on a surface of the optical sensing fibers.

8. The method of claim 1 further comprising providing fluorescence enhancers to enhance fluorescence emission of the fluorophore.

9. The method of claim 8 wherein said providing fluorescence enhancers comprises providing a nanometal particle at a predetermined distance from the fluorophore.

10. The method of claim 9 wherein said providing a nanometal particle comprises providing one of the group consisting of nanogold particles, nanosilver particles, a reagent containing nanogold particles and a reagent containing nanosilver particles.

11. The method of claim 9 wherein said providing fluorescence enhancers further comprises surrounding the nanometal particle with a self-assembled monolayer to maintain the predetermined distance between the fluorophore and the nanometal particle;
   wherein the nanometal particle is dispersed within a solution.

12. The method of claim 1 wherein said providing at least two optical waveguides comprises providing at least two optical sensor fibers coupled to one another in series, and wherein said immobilizing the 1° Mabs on the optical waveguide comprises regenerating the optical sensing fibers.

13. The method of claim 1 wherein said providing at least two optical waveguides comprises providing at least two optical sensor fibers coupled to one another in series, and wherein said immobilizing the 1° Mabs on the optical waveguide comprises coupling a fluorometer to the optical sensing fibers to determine fluorescence emission.

14. The method of claim 1 further comprising selecting the fluorophore from the group consisting of Cyanine 5, AF647, ATTO 647, Bodipy 650/665 and DY-636.

15. The biosensing method of claim 1 further comprising providing a serpentine structure within said serpentine shaped chamber to enhance molecular binding efficiency.

16. The biosensing method of claim 1 wherein the serpentine shaped chamber comprises a bump structure disposed at inner surfaces of the microfluidic channels within the serpentine shaped chamber.

17. The biosensing method of claim 1, wherein the respective microfluidic channels are disposed in parallel to one another and fluidly connected to one another via communication channels.

18. The biosensing method of claim 1, wherein the serpentine chamber has an inlet and an outlet, and wherein said exposing further comprises the sample flowing in sequence through the inlet, over each of the at least two optical waveguides in series, and then through the outlet.

* * * * *